US012629187B2

(12) United States Patent (10) Patent No.: US 12,629,187 B2
Zeuner et al. (45) Date of Patent: May 19, 2026

(54) KIT, PLATE, INSERT, AND METHOD FOR TREATING A CLAVICLE

(71) Applicant: MEDARTIS HOLDING AG, Basel (CH)

(72) Inventors: Hermann Zeuner, Freiburg (DE); Georges Kohut, Fribourg (CH); Cornelia Steiger, Richterswil (CH)

(73) Assignee: MEDARTIS HOLDING AG, Basel (CH)

( * ) Notice: Subject to any disclaimer, the term of this patent is extended or adjusted under 35 U.S.C. 154(b) by 429 days.

(21) Appl. No.: 17/908,589

(22) PCT Filed: Feb. 26, 2021

(86) PCT No.: PCT/EP2021/054887
§ 371 (c)(1),
(2) Date: Sep. 1, 2022

(87) PCT Pub. No.: WO2021/175724
PCT Pub. Date: Sep. 10, 2021

(65) Prior Publication Data
US 2023/0095119 A1 Mar. 30, 2023

(30) Foreign Application Priority Data
Mar. 3, 2020 (EP) .................................... 20160793

(51) Int. Cl.
*A61B 17/80* (2006.01)
(52) U.S. Cl.
CPC ...... *A61B 17/8061* (2013.01); *A61B 17/8047* (2013.01); *A61B 17/808* (2013.01); *A61B 17/8085* (2013.01)

(58) Field of Classification Search
CPC ............ A61B 2017/0414; A61B 17/80; A61B 17/8004; A61B 17/8014; A61B 17/8033;
(Continued)

(56) References Cited

U.S. PATENT DOCUMENTS 6,436,103 B1 * 8/2002 Suddaby ............ A61B 17/1728
606/281
7,837,717 B2 * 11/2010 Deffenbaugh ....... A61B 17/683
606/281
(Continued)

FOREIGN PATENT DOCUMENTS

| DE | 100 39 767 A1 | 7/2001 | |
|---|---|---|---|
| EP | 1 836 981 A2 | 9/2007 | |
| JP | 2012-228612 A | 11/2012 | |
| WO | 2006/099766 A1 | 9/2006 | |
| WO | WO-2019108222 A1 * | 6/2019 | ......... A61B 17/0401 |

OTHER PUBLICATIONS

European Search Report Corresponding to 20160793.4 mailed Sep. 22, 2020.
(Continued)

*Primary Examiner* — Larry E Waggle, Jr.
(74) *Attorney, Agent, or Firm* — Secant IP, PLLC

(57) ABSTRACT
The invention relates to a kit comprising at least one insert (10, 20) and a plate (1) for treating a bone, specifically a clavicle (B). The plate (1) has a receptacle (6) for the insert (10, 20). The insert (10, 20) has an outer contour (C") and/or the receptacle (6) has an inner contour (C), wherein the outer contour (C") and the inner contour (C) fit each other such that the insert (10, 20) inserted into the receptacle (6) can pivot about an axis which runs substantially parallel to a plate top side (0).

17 Claims, 20 Drawing Sheets

(58) Field of Classification Search

CPC .............. A61B 17/8047; A61B 17/808; A61B 17/8872

See application file for complete search history.

(56) References Cited

U.S. PATENT DOCUMENTS

| | | | |
|---|---|---|---|
| 9,005,257 B2 * | 4/2015 | Sun | A61B 17/8047 606/291 |
| 9,149,312 B2 | 10/2015 | Gelfand | |
| 9,579,135 B2 * | 2/2017 | Cook | A61B 17/8047 |
| 10,188,438 B2 * | 1/2019 | Orbay | A61B 17/8052 |
| 10,959,855 B2 * | 3/2021 | Miller | A61F 2/34 |
| 12,290,296 B2 * | 5/2025 | Dong | A61B 17/7041 |
| 2005/0085819 A1 | 4/2005 | Ellis et al. | |
| 2007/0185493 A1 | 8/2007 | Feibel et al. | |
| 2008/0027439 A1 | 1/2008 | Sasing | |
| 2012/0191138 A1 * | 7/2012 | Kiester | A61B 17/8004 606/281 |
| 2016/0074082 A1 * | 3/2016 | Cremer | A61B 17/8004 606/280 |
| 2019/0321182 A1 | 10/2019 | Spenciner | |

OTHER PUBLICATIONS

International Search Report Corresponding to PCT/EP2021/054887 mailed Jul. 6, 2021.

Written Opinion Corresponding to PCT/EP2021/054887 mailed Jul. 6, 2021.

Japanese Office Action Corresponding to 2022-552953 mailed Sep. 3, 2024.

Orthopedic Non-Spinal Bone Plats, Screws, and Washers—Premarket Notification (510(k)) Submissions, Guidance for Industry and Food and Drug Administration Staff, U.S. Department of Health and Human Services, Food and Drug Administration, Center for Devices and Radiological Health, Nov. 22, 2024, 37 pages.

H. Cift et al., Biomechanical comparison of pate-screw and screw fixation in medial tibial plateau fractures (Schatzker 4). A model Study, Orthopedic & Traumatology: Surgery & Research, 96, 2010, pp. 263-267.

Millett, Peter J., Distal Clavicle Fracture Repair—Utilizing a Knotless Coracoid Fixation Device, Video, Jan. 18, 2016, https://www.arthrex.com/resources/VID1-00514-EN/distal-clavicle-fracture-repair-utilizing-a-knotless-coracoid-fixation-device?objectID=human.resource.en.ea74bce2-fa8c-5b27-b868-9e67f7674cee.2&queryID=48673d3315d896163a86e8f39c0541c4.

* cited by examiner

KIT, PLATE, INSERT, AND METHOD FOR TREATING A CLAVICLE

BACKGROUND OF THE INVENTION

Field of the Invention

The invention relates to a kit, a plate and an insert as well as a method for treating a bone, in particular a clavicle, having the features according to the preamble of the independent claims.

Description of Related Art

It is known to treat bones, for example the human clavicle, with implanted plates especially in case of fractures.

US 2007/0185493 discloses a clavicle plate with an overhanging wing for fastening a screw.

US 2005/085819 discloses multi-piece implants for the treatment of bone fractures.

U.S. Pat. No. 9,149,312 discloses a clavicle plate in which an additional body part can be connected to the plate by means of a suture.

However, the known implants and methods have various disadvantages. For example, it is difficult to temporarily fix the plate to be implanted. Furthermore, it is often difficult to connect the plate with a suture. The connection of the plate to the bone by means of bone screws is also not so flexible.

BRIEF SUMMARY OF THE INVENTION

It is therefore the object of the present invention to avoid the disadvantages of the known, and in particular to provide a kit, plate, and/or insert that is easy to implant and therefore inexpensive to use and less prone to error, and at the same time easy to adapt to a patient's anatomy.

According to the invention, these and other tasks are solved with a kit, a plate and an insert as well as the method with the features of the independent claims.

The kit according to the invention comprises at least one insert and one plate for the treatment of a bone, in particular a clavicle. The plate has a receptacle for the insert. The insert has an outer contour, and the receptacle has an inner contour. The inner contour and the outer contour are adapted to each other in such a way that the insert inserted in the receptacle can be pivoted about an axis. The axis runs essentially parallel to the upper side of the plate.

In particular, the insert can be used to create a connection with a bone or other body part. This can be achieved with various connection mechanisms, as detailed below. Particularly advantageous is the connection with a screw or a suture. Since the insert can be pivoted in the inserted state, the anchoring is generally more flexible, since it can also be adjusted during implantation, for example in its orientation.

The insert is preferably configured in such a way that it remains pivotable in the receptacle in the definitive insertion position when a screw or suture is inserted.

In particular, the insert can be pivoted in the receptacle about exactly one axis parallel to the upper side of a plate.

Preferably, the outer contour of the insert and/or the inner contour of the receptacle is at least partially rounded. Additionally or alternatively, the outer contour and/or the inner contour may have an at least partially rotationally symmetrical shape, particularly preferably at least partially a circular cylindrical, stepped cylindrical, conical, elliptical, hyperbolic or parabolic shape, particularly in a cross-section perpendicular to a longitudinal axis.

An at least partially, preferably completely, rotationally symmetrical structure of inner contour and/or outer contour perpendicular to a longitudinal axis is advantageous for precisely defined attachment of the insert, which at the same time permits precisely defined pivoting. Thus, the insert can be inserted quickly and reliably, since the top side and bottom side of the insert preferably do not differ in such a rotationally symmetrical insert. Thus, the insert cannot be placed laterally reversed in the receptacle. Alternatively, the upper and lower sides of the insert can also differ, i.e. only one direction of correct placement is possible.

In addition, the insert is preferably shaped so that the insert can be completely arranged in the receptacle of the plate.

Thus, the insert can be arranged flush and/or lowered to the plate in the receptacle. Thus, the plate does not have any unevenness due to the insert.

In addition, this arrangement allows the plate to be placed flush with the bone, regardless of the positioning of the insert. Thus, fixation, especially temporary fixation, can be carried out more easily.

A partially rounded shape shall in particular include shapes which have a circular cross-section, for example along a longitudinal axis. Likewise, all shapes that are formed along a surface without edges and that are not straight are to be understood as rounded.

Such shapes make it particularly easy to pivot the insert in the receptacle.

Preferably, the outer contour and the inner contour are adapted to each other in such a way that the insert inserted into the receptacle is displaceable in a longitudinal direction of the plate. The displacement is in particular such that the insert can be inserted stably in different positions along the longitudinal direction. For this purpose, the receptacle has a support surface, in particular in the longitudinal direction, which runs parallel to the underside of the plate and is longer than the dimension of the insert in the longitudinal direction.

This allows for further customization of the anchoring of the plate and insert to a body part, such as a bone.

The displaceability allows an anchoring to be flexibly adapted to the shape of a body part, such as a bone. Thus, the size or curvature of a bone, such as the clavicle, can be taken into account in the anchoring. In addition, flexible attachment of an anchoring can avoid stress between anchorings.

Preferably, the insert is adapted to fix a suture and/or to receive a screw.

According to a first aspect of the invention, the insert preferably comprises at least one strut adapted to hold a suture. Particularly preferably, the insert comprises exactly one strut.

This makes it possible to attach a suture to the insert in a particularly simple manner, for example by means of a knot or loop. In particular, a strut can also be arranged within a through-opening so that a suture can be arranged through the insert. In particular, this also allows the bone plate to be anchored to a body part.

Preferably, the strut is sunk. Sunk strut means that the strut is arranged inside the opening in such a way that it is not flush with the surface of the insert on at least one side. Therefore, a sunk strut is usually made thinner than the insert. However, it may be arranged flush against the surface of the insert on one side. Alternatively, it can be arranged inside the opening in such a way that it is sunk when viewed from both sides of the opening, i.e. it is not arranged flush with any surface of the insert.

The through hole is preferably located on the insert in such a way that when the insert is properly placed in the receptacle, there is a passage for receiving a suture or screw from the top of the plate to the bottom of the plate.

The opening of the insert in the receptacle can preferably be arranged on the top of the plate.

Thus, the insert can be easily fixed by a screw and/or suture.

In particular, this allows a node to be sunk into the insert, which can lead to a reduction in irritation of tissue. Preferably, the kit comprises a suture for fixation of a body part. Particularly preferably, the suture is adapted for fixing a coracoid.

Alternatively, according to a second aspect of the invention, the insert comprises an opening for receptacle of a screw, in particular a bone screw.

In particular, the opening can be designed with a thread. However, it is also possible to use a threadless opening.

In particular, the opening can be a bore that is essentially cylindrical and shaped with a circular cross-section. Alternatively, other cross-sections of the opening are conceivable, such as square, elliptical, triangular or rectangular. The cross-section along an axis perpendicular to the axis of the hole can also be round, elliptical, rectangular, square or rectangular, in particular if the opening is designed as an elongated hole. It is also conceivable to design the opening as an interlocking hole.

This allows the insert to be attached to a bone with the screw. This allows further anchoring of the plate to a bone. The pivotability of the insert in particular also allows the angle of entry of the screw into the bone to be adjusted.

Preferably, the kit comprises at least one screw, in particular a non-locking screw. Alternatively, the screw can also be locking. Particularly preferably, the screw is adapted to the opening of the insert in such a way that it can be screwed in through this opening. In particular, the screw diameter can be adapted to an inner diameter of the opening of the insert and/or the external thread of the screw can be adapted to an internal thread or a locking contour in the opening of the insert.

The screw can be screwed through the internal thread or the locking contour in the opening of the insert and the external thread of the screw can be screwed into the bone. A locking contour on the head of the screw then anchors into the mating contour of the insert. Thus, the screw can be firmly locked to the insert and fixed to the bone at the same time.

The screw may also include a screw head that is sized to not fit through the opening. If the opening is designed accordingly, the screw head can also be shaped and sized so that it can be sunk into the opening of the insert. It is also conceivable to shape the screw head as a locking head.

Preferably, the insert has a holder. The insert and the holder are connected to each other via a predetermined breaking point. This allows the insert to be easily held and inserted into a receptacle in the desired position. The predetermined breaking point allows the insert to be removed from the holder at a desired time, e.g. after insertion into the receptacle. The holder can also be designed in such a way that, in addition to holding, it also serves to simultaneously suture the suture.

Preferably, the plate has at least one recess on its top side which does not penetrate the plate. This is adapted for temporary reception of a tool, preferably pliers.

Preferably, the kit comprises a tool, particularly preferably a pair of pliers. The tool comprises at least one tip, the shape and size of which is adapted so that it can be brought into operative contact with the recess of the plate.

The invention further relates to an insert. The insert is particularly suitable for use in a kit as described above. The skilled person therefore understands that all the properties described herein can also be applied in the kit. Likewise, all of the properties of the insert described above can be used as part of the kit in addition or alternatively for a single insert. The insert is adapted for receptacle in a bone plate and includes at least one opening. The opening is adapted for receptacle of a screw and/or for fixation of a suture. The insert is also connected to a holder via a predetermined breaking point.

The insert is particularly preferably partially rounded. It is also possible to design an insert with a rotationally symmetrical cross-section perpendicular to the longitudinal axis. It would also be conceivable that the cross-section of the insert has an n-fold rotational symmetry, where n can be any integer greater than 2, particularly preferably at least 3. For example, a rectangular cross-section is also conceivable.

Preferably, the insert includes a strut disposed within the opening and, in particular, sunk therein.

Preferably, the at least one opening is adapted to receive a screw. Preferably, the thread diameter of the screw is 1 to 8 mm, more preferably 2 to 5 mm, even more preferably 2.5 to 3.5 mm.

The invention further relates to a plate for treating a bone, in particular a clavicle. The plate is particularly suitable for use in a kit as described above. It is also clear to the person skilled in the art that all the features of a plate described above, in connection with the kit, can also be used for the plate according to the invention. The plate comprises at least one screw hole for receptacle of a bone screw. The plate has at least one overhanging tab in an end region.

The tab is particularly suitable for shaping to the individual anatomy and for fixation to a bone or other body part. It therefore allows fixation from different angles or positions, which makes treatment more flexible.

Preferably, the plate comprises at least one, more preferably at least two, even more preferably exactly two, tabs.

Preferably, the at least one tab is connected to the plate via at least one bendable bridge. In particular, the tab has a receiving opening for a bone screw.

This allows the plate to be attached to a bone by means of a bone screw. In particular, the bridge can be adapted to the bone in different positions and/or orientations, so that a screw can be inserted into the bone in different positions and/or orientations. This enables a particularly advantageous treatment that can be specifically adapted to the patient's anatomy if required.

If the bone structure is very poor, there is a risk of screw tear-out. By means of the above-mentioned tabs, screws can additionally be placed from other directions and thus prevent these screw tear-outs.

It is also conceivable that a lug is connected to the plate by two or more bridges. For example, one tab can be connected to the plate via a double bridge.

The term bendable shall include at least sufficient ductility of the material so that the material is plastically deformable without breaking. In particular, bendable shall also be understood in such a way that plastic deformation can be achieved by means of hand tools or by hand alone, for example by suitable material selection or dimensioning of the corresponding part.

Preferably, the plate has a greater plate thickness in the area of the screw hole or receptacle than in the area of the bridge.

Preferably, the tab and/or the bridge is shaped such that an angle between a longitudinal axis of the receiving opening for a bone screw and a normal to the surface of the plate is at most 150°. Particularly preferably, the angle is at most 120°, even more preferably at most 90°.

The invention further relates to a plate for the treatment of a bone, in particular the clavicle. The plate is particularly suitable for use in a kit as described above. It is also clear to the person skilled in the art that all the features of a plate described above in connection with the kit can also be used for the plate according to the invention. Likewise, all the features described above in connection with a plate can be combined with the plate described herein. The plate has at least one screw hole for receiving a bone screw. The plate further has a top side and a bottom side, wherein the bottom side of the plate is shaped to at least partially be in contact with a bone. The top side of the plate has at least one recess that does not penetrate the plate and is adapted to temporarily receive a tool. Typically, the tool is a surgical instrument known to the skilled person.

A temporary receiving is used to create a form and/or force fit with a tool that temporarily prevents or hinders displacement of the tool relative to the bone plate.

The plate can therefore be held in a particularly simple manner by means of a tool, which makes treatment easier and safer because the surgeon can prevent the plate from moving relative to the bone. In particular, the plate can be held without blocking a screw hole because a tool is placed in it. Furthermore, holding the plate in a recess adapted for this purpose allows the plate to be held without play. In contrast, a plate held in a screw hole with a tool is somewhat movable, which can make treatment less secure and more cumbersome for the surgeon.

Preferably, the at least one recess is arranged, with respect to a longitudinal direction of the plate, between screw holes, particularly preferably midway between screw holes.

This allows the plate to be held adjacent to a point where a screw is to be inserted, for example, if desired. This minimizes the risk of slipping at the site of the screw hole used and makes the treatment safer.

Preferably, the at least one recess on the plate surface is substantially midway to an outer boundary of the plate as viewed in a transverse direction perpendicular to the longitudinal direction.

As a result, when the plate is held by means of a tool inserted into the recess, it is kept close to its center of gravity. This reduces the risk of slippage and makes treatment safer.

However, recesses are of course also conceivable that are close to the edge of the plate or close to a plate hole.

Preferably, the recess has a longitudinal axis and is shaped substantially rotationally symmetrically with respect to the longitudinal axis.

Rotational symmetry should in particular also include n-fold rotational symmetries, where n can be any integer, preferably an integer which is at least 2, particularly preferably at least 3. For example, recesses with a square or triangular cross-section in the plate plane are also conceivable.

The recess can be shaped as a cylinder with any rotationally symmetrical base surface. For example, it is conceivable to shape the recess as a cylinder with a square or triangular base. Alternatively, the recess can also be shaped as a pyramid, whereby the base area can also be basically arbitrary. A recess shaped as a cone is also conceivable.

However, it is not necessary for the recess to be shaped conically or cylindrically. Spherical or ellipsoidal shapes are also conceivable, especially if the cross-sectional area of the recess in the plate plane is circular or elliptical.

Alternatively, the recess is shaped as an elongated shape. This allows the tool to be guided in the recess along a longitudinal axis of the recess and the plate to be moved accordingly without having to remove the tool from the recess.

Preferably, the recess has a depth of 0.01 to 2 mm, more preferably 0.1 to 1 mm, even more preferably 0.2 to 0.5 mm.

Preferably, the at least one recess in at least one direction parallel to the surface of the plate has a size in a range of 0.1 to 3 mm, more preferably 0.5 to 1.5 mm, even more preferably 0.8 to 1.2 mm.

In particular, for non-circular recesses, the shortest side wall may have a value in the ranges mentioned.

In particular, the at least one recess in a direction in the plane of the panel surface may have a value in said ranges.

Preferably, the plate is adapted in size and shape to a bone, in particular a human clavicle.

Preferably, therefore, the plate has a length of 30 to 150 mm and a width of 6 to 40 mm. The plate can be at least partially curved in a plane parallel to the plate surface. In particular, the radius of curvature may be 30 to 250 mm.

Preferably, the plate comprises and particularly preferably consists of a biocompatible material. In particular, the biocompatible material may be selected from a group of implant steel, titanium, titanium alloys, ceramics and plastics. Particularly suitable plastics include polyetheretherketone (PEEK), UHMW polyethylene (PE-UHMW), polypropylene (PP), and polyethylene terephthalate (PET).

The invention further relates to a method for treating a bone, in particular a clavicle, preferably a human clavicle. In particular, the method can be carried out with a plate and/or an insert or a kit as described above.

Z Firstly, the method comprises providing a plate.

Preferably, the plate comprises at least one tab and/or a bridge connected to the tab, the tab and/or the bridge being arranged on the plate. Preferably, the tab and/or the bridge is therefore bent to the bone in a further step.

Preferably, the plate is held in place by means of a tool, in particular at least temporarily fixed to the bone. In particular, pliers can be used. The tool is preferably introduced in a recess which does not traverse the plate, wherein the cross-sectional area of the recess, in particular in the plate plane, is adapted to a diameter of a tip of the tool.

Further, the plate is attached to a clavicle by means of at least one screw that is sutured into the clavicle through a screw hole in the plate.

Preferably, a further screw is screwed into the clavicle through at least one tab, in particular through a receiving opening for a screw in the tab. In particular, the tab can be connected to the plate by means of a flexible bridge. Additionally or alternatively, two or more screws are screwed into the clavicle in this way through one tab or several tabs each. Particularly preferably, a total of two screws are screwed in through one tab each.

Preferably, an insert is inserted into a receptacle of the plate adapted for this purpose. The insert can be connected to a holder via a predetermined breaking point. Particularly preferably, the insert is inserted by means of the holder and the method may further comprise a step in which the holder is removed by breaking the predetermined breaking point. The insert may further be pivoted about an axis substantially parallel to a top of the plate. In particular, a suture may be passed through an opening of the insert, the suture being connected to a body part, preferably a coracoid. In particular, after passing through the opening of the insert, the suture may be connected to a strut provided therefor, in particular by a knot. Another screw can be screwed into the clavicle through an opening of the insert. Alternatively, a suture can be connected to a body part, preferably to a coracoid, via a strut provided for this purpose in an opening of the insert and fixing of the suture. This allows the body part to be stabilized.

BRIEF DESCRIPTION OF THE DRAWINGS

The invention is explained in more detail below with reference to the figures and embodiments, showing:

FIGS. 1a-1c: a perspective view of a first embodiment of a clavicle plate and cross-sectional views of this plate perpendicular to a longitudinal direction.

FIGS. 14a-14h: the steps of a method for using the insert of FIG. 12l.

DETAILED DESCRIPTION OF THE DRAWINGS

For the sake of clarity, identical features within a figure are not repeatedly marked with the same reference signs.

Figure 1A:
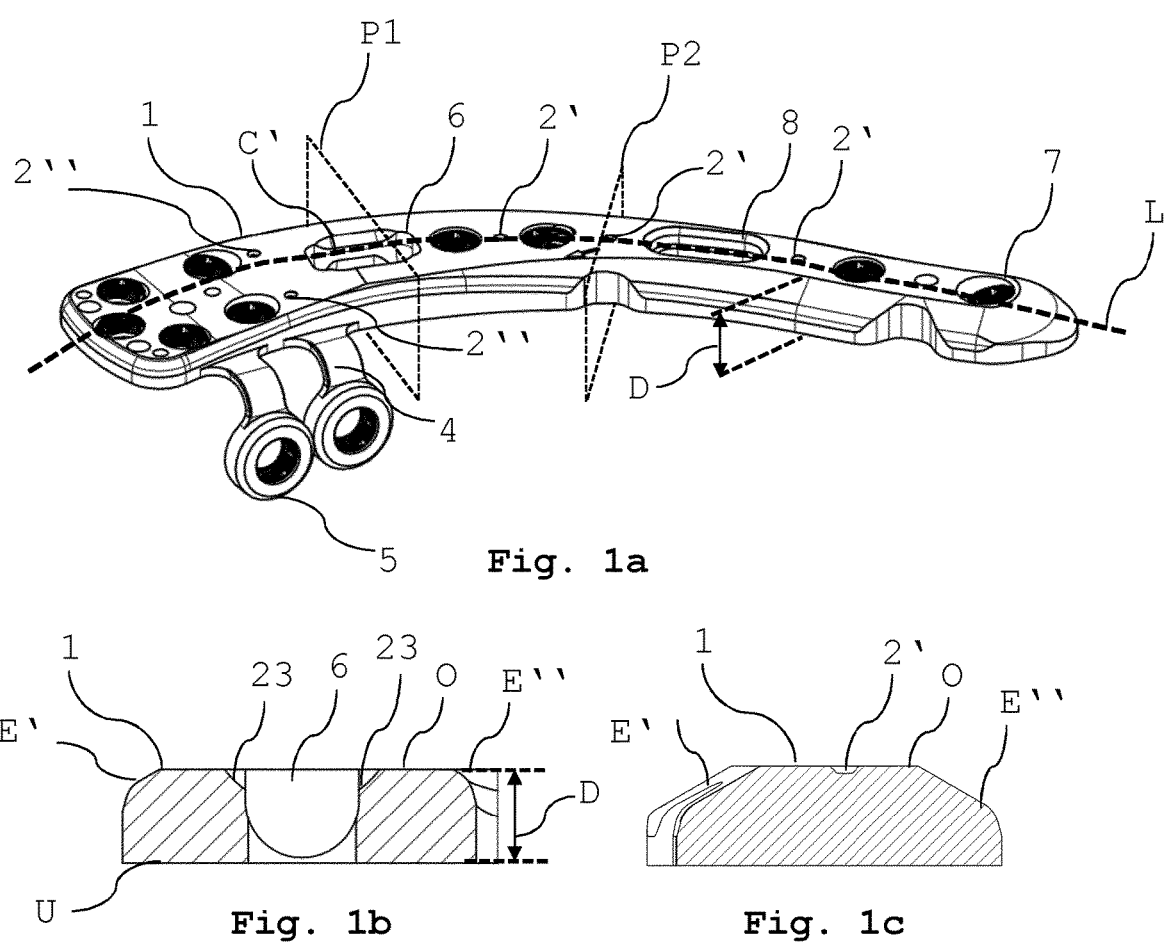

FIG. 1a shows a clavicle plate 1 in perspective view. The plate 1 is curved along a longitudinal direction (L) to conform to the shape of a human clavicle. The plate has nine round screw holes 7. In addition, the plate 1 has an elongated hole 8 arranged substantially along the longitudinal direction (L). The elongated hole 8 is suitable for receiving a conventional bone screw. Furthermore, the plate 1 comprises a receptacle 6 for an insert (10, 20 in the following figures). The receptacle has a contour C', which is partially rounded. In the present case, the rounding is designed as a circular arc-shaped cross-section in a plane P1 perpendicular to the longitudinal direction (L) (see FIG. 1b).

The plate has recesses 2', 2" on its top side. In the plate shown here, some recesses 2' are arranged along the longitudinal direction midway between two screw holes 7,8 each. Seen in a direction perpendicular to the longitudinal direction (L), these recesses 2' are arranged midway between the plate edges. Further recesses 2" are arranged in the vicinity of screw holes 7, but not midway in relation to the longitudinal direction (L) or in a direction perpendicular to the longitudinal direction.

The recesses have a circular shape. The diameter of the recesses 2', 2" in the plane O (see FIG. 1c) is 1 mm. The thickness D of plate 1 varies along the longitudinal direction (L). It is smaller at the ends of the plate 1 and increases along the longitudinal direction (L), reaching a maximum in the area of the receptacle 6.

The plate 1 further comprises two tabs 5, each of which is connected to the plate 1 via a bridge 4. The tabs 5 are annular in shape and are therefore suitable for receiving a screw. The bridges 4 have a rectangular cross-sectional profile. They can therefore be bent only insignificantly in a direction parallel to the longitudinal direction (L) and only with great force. Perpendicular to the longitudinal direction (L), however, the bridges 4 are bendable. In the embodiment shown, the tabs 5 are arranged such that a screw inserted into the tab 5 is substantially perpendicular to the longitudinal direction (L) and parallel to the plate surface. However, by bending the bridges 4, it can be achieved that an inserted screw would be arranged at an angle not equal to 0° to the plate surface. Due to the insignificant bendability in the direction of the longitudinal direction (L), screws inserted into the tabs 5 remain stable against transverse forces even when the bridges 4 are bent. The plate is made of titanium or a titanium alloy.

FIG. 1b shows a cross-sectional view of the plate 1 of FIG. 1a along the plane P1. The receptacle 6 intersects the plane P1. In cross-section, the plate has a straight bottom side U and a top side O running parallel thereto. As already explained in connection with FIG. 1a, the plate thickness D along the longitudinal direction L is not constant. The top side O and the bottom side U are partially arranged at an angle to each other in the direction of the longitudinal direction L (see FIG. 1a, left of plane P1). The receptacle 6 is partially rounded in shape and includes recesses 23 whose surface is concavely curved and has a radius of curvature of about 3.5 mm. The recesses connect the side wall of receptacle 6 to the top side O and are arranged at an angle of about 45° on both sides. Rounded edges E', E" are also arranged on the top of the plate.

FIG. 1c shows a cross-sectional view of the plate 1 of FIG. 1a along the plane P2. A recess 2' is arranged on the top side O midway between the edges E', E". The recess 2' is designed as a truncated cone so that it has a trapezoidal cross-section. The depth of the recess is 0.3 mm. The diameter of the base surface of the cone in the plane O is 1 mm, as mentioned above. The recessed surface of the recess has a diameter of 0.6 mm.

Figure 2:
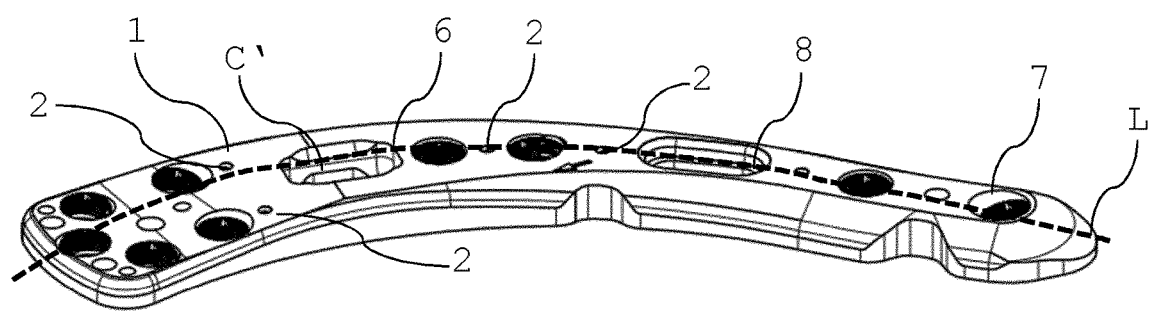
FIG. 2: a perspective view of a second embodiment of a clavicle plate.

FIG. 2 shows an alternative embodiment of a clavicle plate 1, which is similar to the plate 1 shown in FIG. 1*a*. Unlike the plate 1 shown in FIG. 1*a*, the present plate shown does not have tabs (4 in FIG. 1*a*) or bridges (5 in FIG. 1*a*).

Figure 3A:
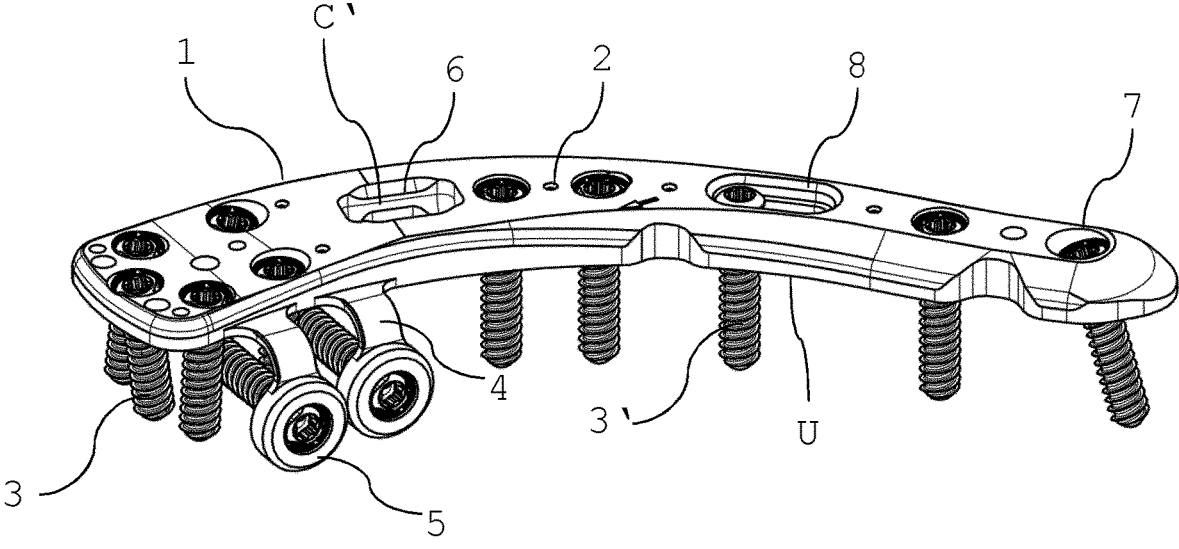
FIGS. 3a+3b: a perspective view of the clavicle plate of FIG. 1 with inserted screws in a side view and a bottom view.

FIG. 3*a* shows the clavicle plate of FIG. 1*a* with screws 3 inserted in the screw holes 7 in a perspective view. In the present embodiment shown, the screw holes are of variable angle design so that the screws can each be oriented in an angular range. Such variable-angle holes are disclosed, for example, in WO 2006/099766. Alternatively, however, it would also be possible to design the screw holes as conventional, essentially cylindrical bores with an internal thread. In this case, the orientation of the screws 3 would correspond substantially to the orientation of a longitudinal axis of the holes. Furthermore, a non-angularly stable screw 3' is inserted in the oblong hole 8. The screw head thereof is displaceably mounted in oblong hole 8, so that relative to screw 3' the plate can be displaced along oblong hole 8. A screw 3 is inserted in each of the tabs 5. The tabs 5 are each connected to the plate via a bridge 4 and have not been bent compared to the embodiment shown in 1. Therefore, in the embodiment shown, the screws are oriented parallel to the underside U of the clavicle plate 1.

Figure 3B:
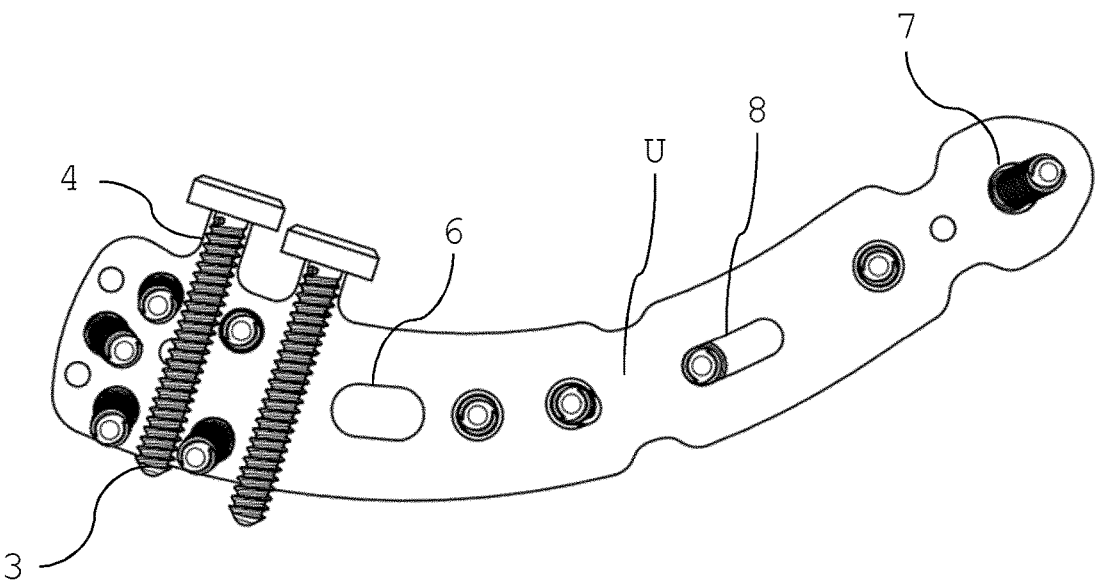
Figures 4, 5A, 5B, 5C, 5D:
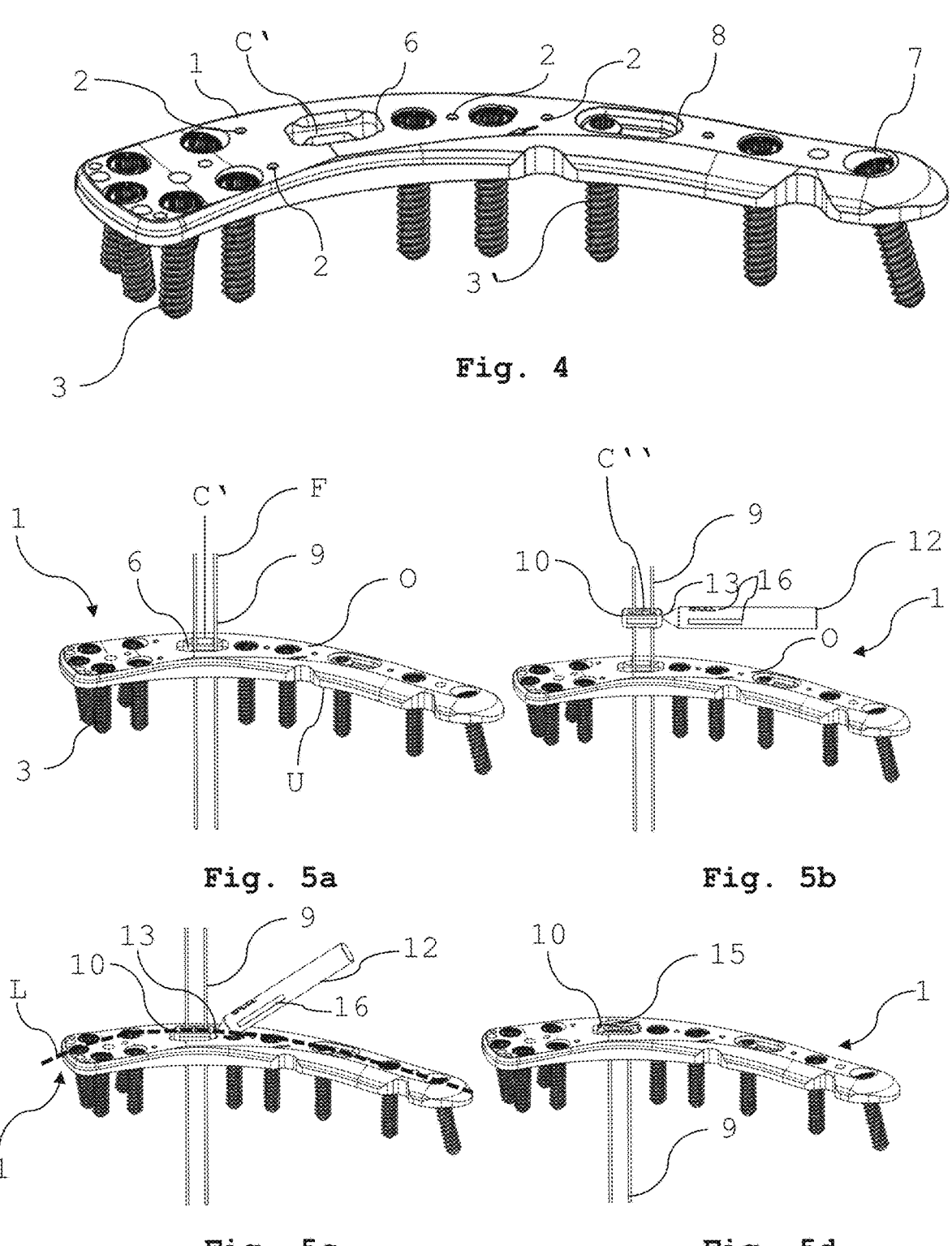
FIG. 4: a perspective view of the clavicle plate of FIG. 2 with inserted screws in a side view.
FIGS. 5a-5c: illustration of the steps of a method for fixing an insert to a suture.

FIG. 3*b* shows a bottom view of the clavicle plate 1 from FIG. 3*a*. The transverse screws from the tabs pass between the other screw axes without touching them. These transverse screws allow a reduction of the risk of screw break-out in poor quality bone. FIG. 4 shows the clavicle plate 1 of FIG. 2*a* with screws 3 inserted in the screw holes in an oblique view. The screw holes 7 are designed here for variable-angle receptacle of screws and as shown, for example, in WO 2006/099766. The screws 3 can be screwed in at an angle range of +/−15° relative to a neutral position. Of course, one or more screw holes 7 could alternatively be shaped in a non-variable angle. The screw 3' in the oblong hole 8 is displaceably mounted and not angularly stable so that it can be displaced along the longitudinal direction of the plate.

FIGS. 5*a*-5*d* show a method of using an insert 10 with a clavicle plate 1 as shown in FIG. 2*a*. Of course, the same procedure could be performed with other embodiments of the clavicle plate and/or other than the insert 10 shown here and/or on a different bone. Furthermore, the plate 1 is shown without bone for overview purposes (see FIGS. 20*a*+20*b*). However, the procedure could of course be performed after the screws 3 have been screwed into a bone.

FIG. 5*a* shows how a suture 9 is first fed through the receptacle 6. The suture 9 can be made of UHMWPE. The suture 9 has two free ends F, which are guided through the receptacle 6 from the underside U of the plate.

FIG. 5*b* shows how the suture 9 is then guided through an insert 10. The insert 10 is adapted for fixing to a suture 9 and has a sunk strut (not visible) and a rounded outer contour C″ for this purpose. The insert 10 is connected to a holder 12 via a predetermined breaking point 13 (see FIGS. 6*a*-6*c*). The holder has two markings 16 which, on the one hand, indicate to the user which side of the insert 10 should point in the same direction as the top of the plate O when inserted and, on the other hand, has a serial number. The latter can be retained during treatment and thus enables easier documentation of the treatment. This reduces the error rate and thus increases the safety of the treatment. The suture 9 is passed through the insert 10 with one end F on each side of the strut (see, for example, FIGS. 6*a*+6*b*).

FIG. 5*c* shows how the insert 10 is guided into the receptacle 6 of the clavicle plate with the aid of the retainer 12. The retainer 12 can be removed from the insert 10 by breaking the predetermined breaking point 13 by bending. The retainer 12 can be stored after removal and allows the inserted insert to be identified at a later time via the marking 16, which includes a serial number. In the present case, the inner contour C' of the receptacle 6 is partially shaped and the outer contour C″ of the insert 10 is shaped entirely circular-cylindrical in cross-section, whereby the insert 1 can be pivoted in the receptacle 6 about the axis of the insert 1 and/or the receptacle 6.

Figure 6A:
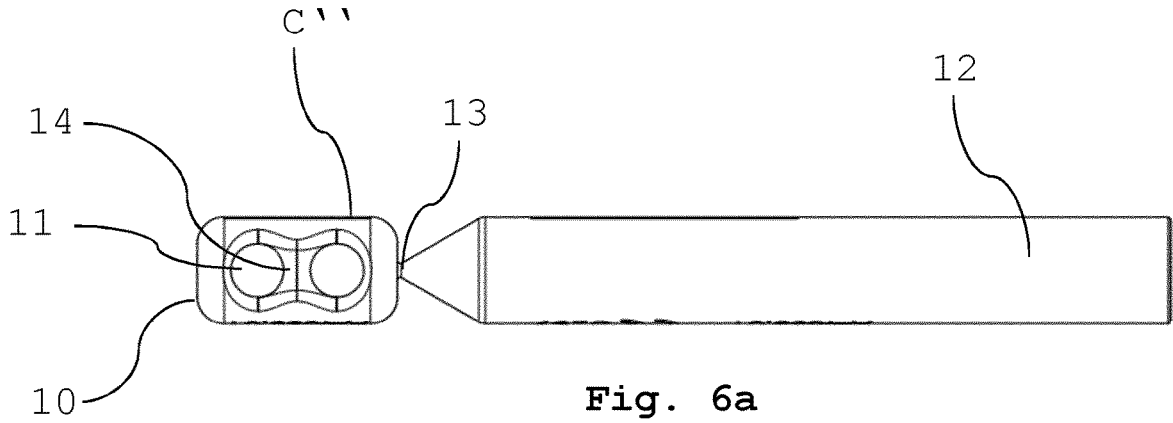
FIGS. 6a-6e: a first embodiment of an insert for suture fixation from different perspectives and in a cross-section along a longitudinal axis.
Figure 6B:
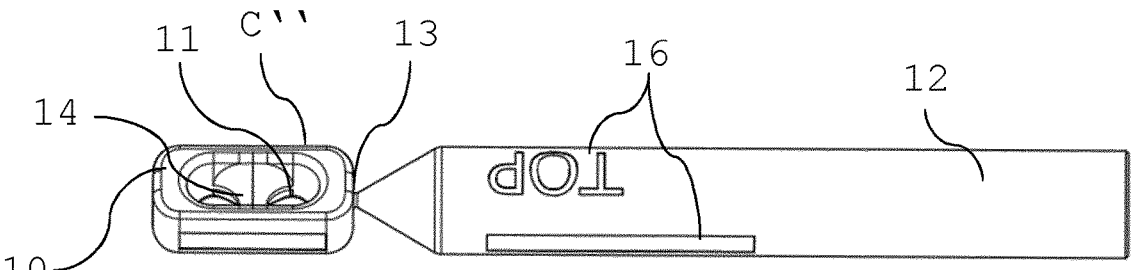

FIG. 5*d* shows how the suture 9 is finally attached to the insert 10 by a knot 15. It is also conceivable to use several knots. If the suture 9 is attached to a coracoid, for example via a further knot or via a loop, this is connected via the insert 10 of the clavicle plate 1 so that the distance between the coracoid and the clavicle is kept constant and physiologically correct. FIG. 6*a* shows a bottom view of an insert 10 as it can be used in the process according to FIGS. 5*a*-5*d*. The insert 10 is adapted for fixing with a suture and therefore has a strut 14, which is sunk and forms two openings 11 through which a suture 9 can be passed so that it can be connected to the strut 14 by means of a knot or loop. The insert 10 is connected to a holder 12 via a predetermined breaking point 13. The insert 10 is made of a titanium alloy and is integrally connected to the holder 12. FIG. 6*b* shows the insert of FIG. 6*a* in a perspective view. The holder 12 has two markings. On the one hand, a marking with "TOP" indicates that this side should point in the same direction as the top side of the plate 1 when inserted into a receptacle 6 of a clavicle plate 1. On the other hand, a second marking 16, for example in the form of a serial number or a bar code, is provided, which serves to identify the insert 10 before, during, and after its use.

Figure 6C:
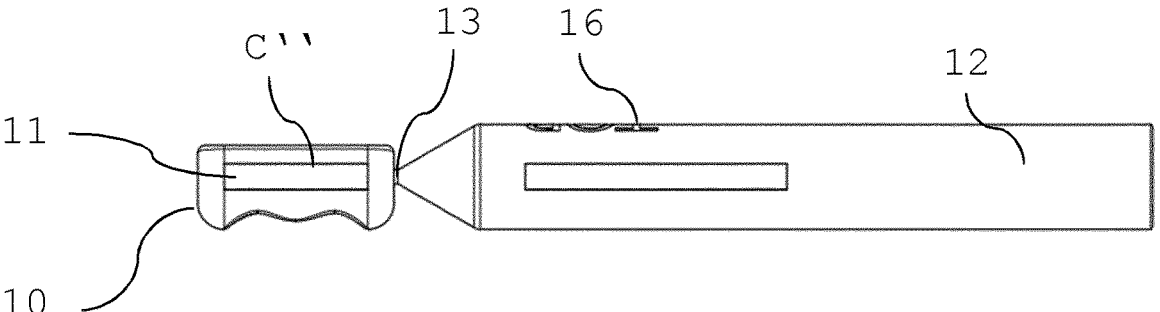

FIG. 6*c* shows the insert 10 of FIGS. 6*a* and 6*b* in a side view.

Figure 6D:
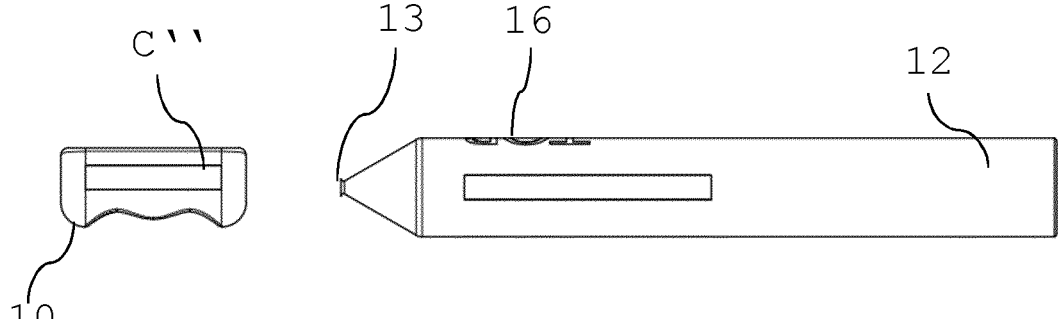

FIG. 6*d* shows the insert 10 of FIGS. 6*a*-6*c* in the same side view as in FIG. 6*c*. The predetermined breaking point 13 is broken, so that the insert 10 and the holder are no longer connected to each other.

Figure 6E:
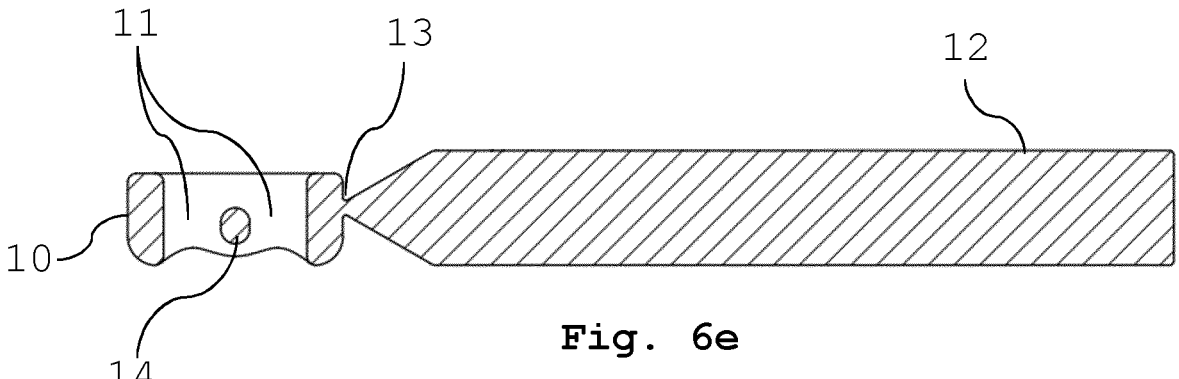

FIG. 6*e* shows the insert of FIG. 6*c* in a cross-sectional view along a longitudinal axis of the insert 10 and the holder 12. The strut 14 is sunk and forms two openings 11 through which a suture 9 can be passed.

Figure 7:
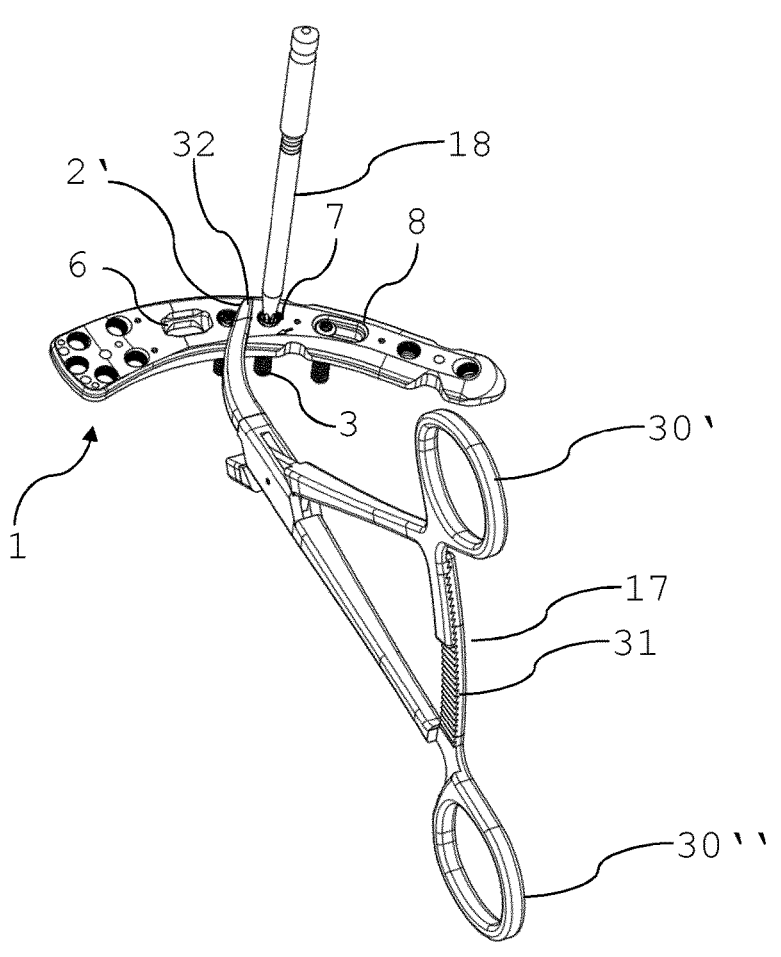
FIG. 7: the use of a tool for holding the clavicle plate of FIG. 2.

FIG. 7 schematically shows the holding of a clavicle plate 1 by means of a tool 17. The tool 17 in the present case is a surgical plier comprising a handle 30',30″ which can be gripped with two fingers. The pliers 17 further comprise a locking ratchet 31 and at least one tip 32. The tip 32 can be inserted into a recess 2' and is therefore prevented from moving relative to the plate 1 by means of a positive fit. Furthermore, by means of the engagement ratchet 31, the opening of the pliers can be locked in this position so that the plate is temporarily fixed and a user, e.g. a physician, does not have to hold the pliers for further treatment. This leaves his hands free, for example, to screw a bone screw 3 through a screw hole 7 into the bone by means of a screwdriver 18.

Figures 8A, 8B:
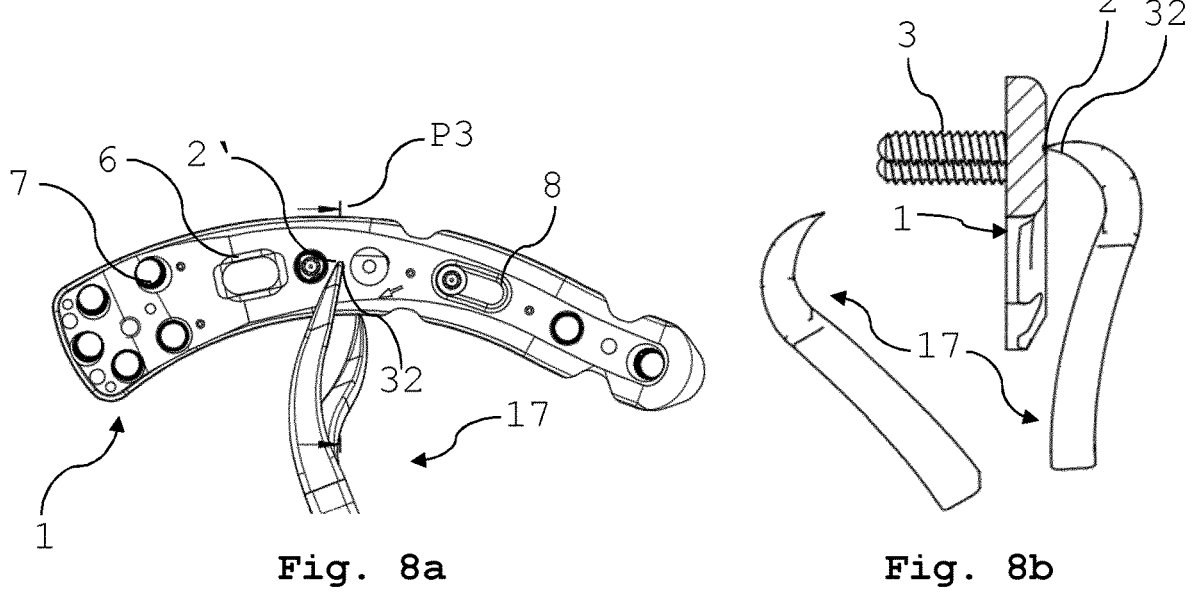
FIGS. 8a-8d: the clavicle plate of FIG. 7 in a top view and in a cross-section perpendicular to the longitudinal direction, and in 8c-8d a method not according to the invention for holding the clavicle plate of FIG. 2 with a tool.

FIG. 8*a* shows a top view of the tip 32 of a tool 17 inserted 6 into the recess 2' as shown in FIG. 7. Since the pliers are placed in the recess 2' between plate holes, a bone screw can be screwed into these plate holes without any problems.

FIG. 8*b* shows a cross-sectional view of the tool 17 and the plate 1 along the plane P3 of FIG. 8*a*. The tool includes two tips 32 that are substantially identical in design. Thus, the tool 17 can be inserted into a recess 2' with both tips 32. Alternatively, it would also be possible to implement one side of the tool with a different end. For example, a shallow gripper could be used to allow tissue to be gripped while reducing injury to that tissue.

Figures 8C, 8D:
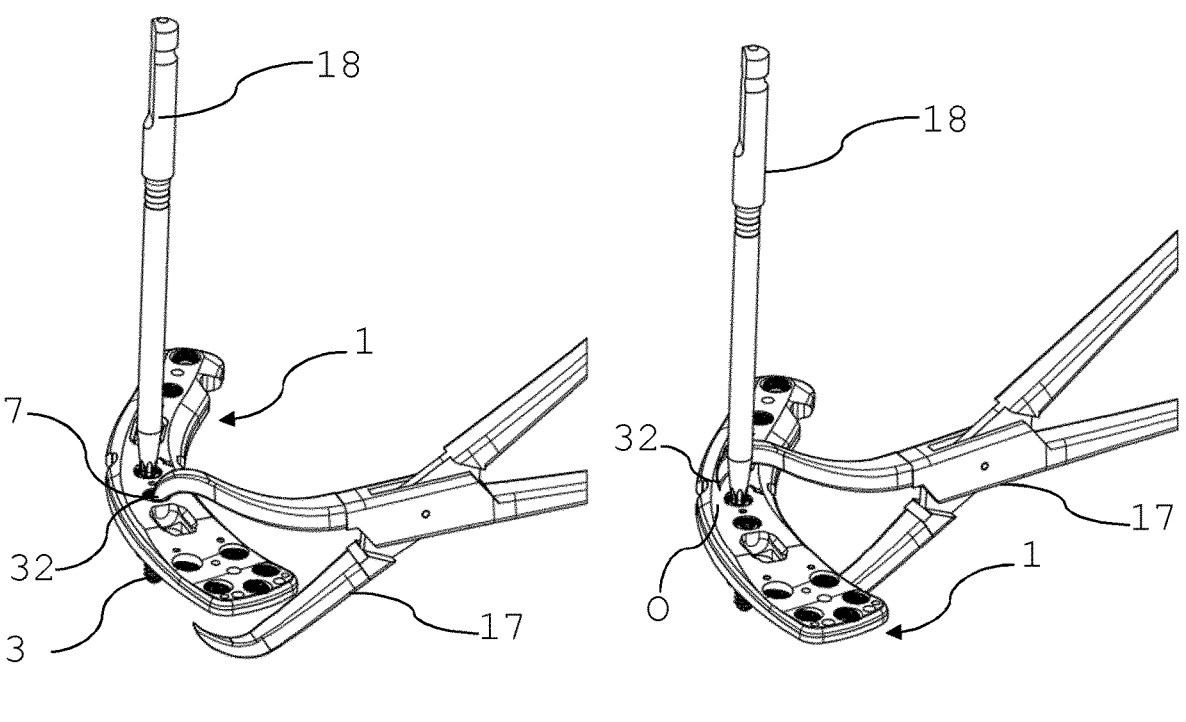

FIG. 8c shows a method not according to the invention for holding a plate 1 with a tool. Here, a tip 32 of the tool is inserted into a screw hole 7 to temporarily fix the plate 1. It is true that this restricts the movement of the plate 1 relative to the tool 17. However, some movement is still possible because the screw hole 7 has a size and shape not adapted to the tool 17. Furthermore, no screw 3 can be inserted into the used screw hole 7, at least temporarily.

FIG. 8d shows another method not according to the invention for holding a plate 1 with a tool. Here, the tip 32 is placed on the top of the plate O. The plate 1 and the tool 17 are connected only by a frictional connection. The plate 1 can therefore easily slip. In addition, the tip 32 and the plate can become damaged, e.g. scratched.

Figure 9A:
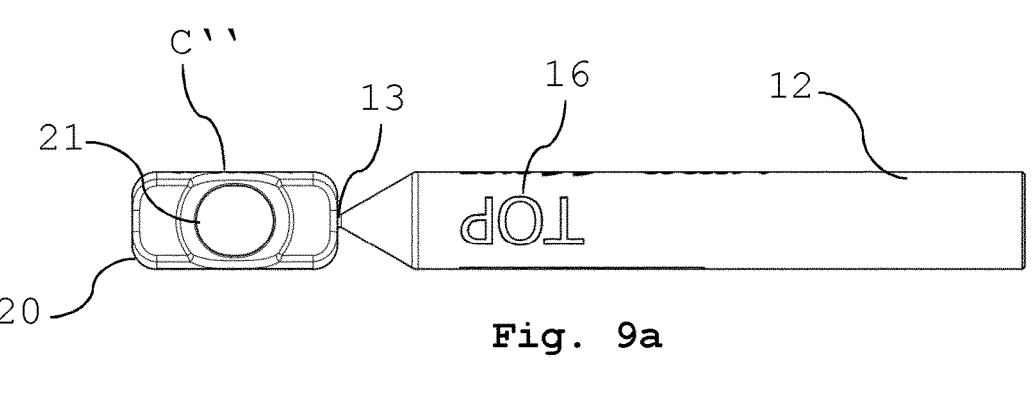
FIGS. 9a-9e: a second embodiment of an insert to receive a screw in different perspectives and in a cross-sectional view along a longitudinal axis.

FIG. 9a shows a second embodiment of an insert 20 in a top view. The insert is adapted to receive a screw. For this purpose, it has an opening 21 into which a screw can be inserted. The insert 20 is connected to a holder 12 via a predetermined breaking point 13, which has two markings 16. The holder 12 corresponds essentially to the holder of FIG. 6a.

Figure 9B:
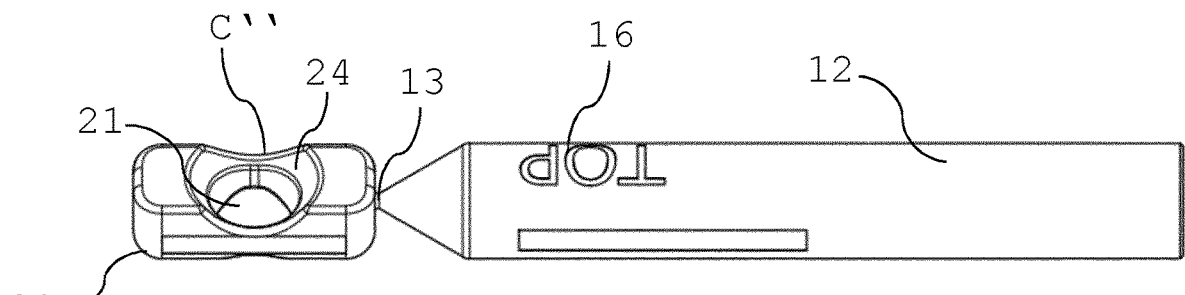
Figure 9B:

FIG. 9b shows the insert 20 of FIG. 9b in perspective view. The opening 21 for the receptacle of a screw is designed here without a thread. However, it would of course be conceivable that the opening has an internal thread or another contour for the angularly stable receptacle of a screw, in particular a receptacle according to WO 2006/099766. The opening has an essentially cylindrical shape and is also designed as a blind hole 24.

Figure 9C:
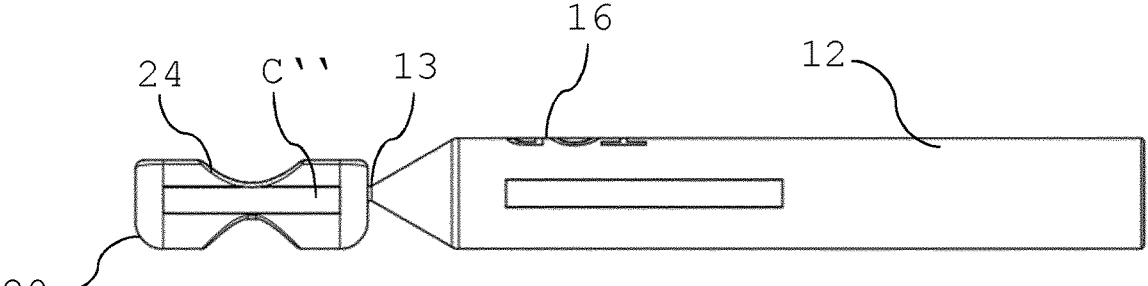

FIG. 9c shows the insert of FIGS. 9a and 9b in a side view. The blind hole 24 is shaped in such a way that the insert 20 has depressions in a side view.

Figure 9D:
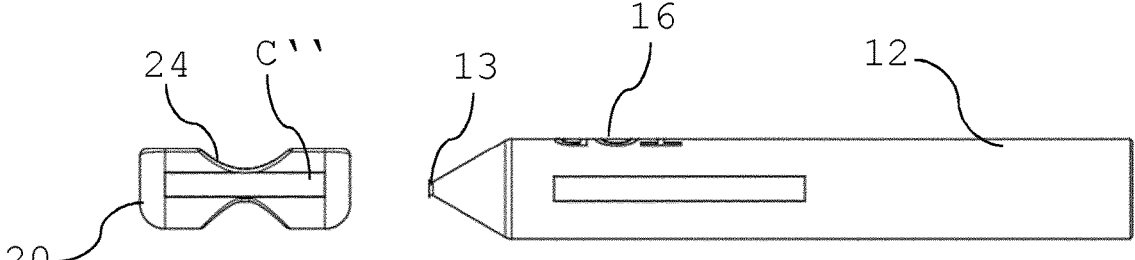

FIG. 9d shows the insert 20 of FIGS. 9a-9c, where the predetermined breaking point 13 has been broken and the holder 12 is therefore separated from the insert 20.

Figure 9E:
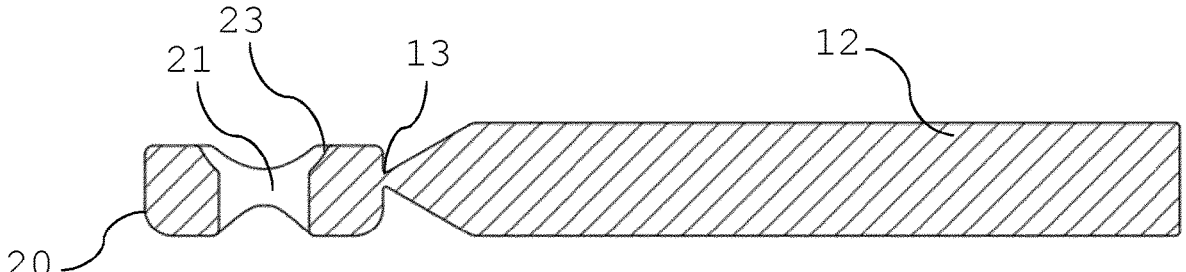

FIG. 9e shows the insert of FIGS. 9a-9d in a cross-sectional view along the longitudinal axis of the holder 12 and the insert 20.

FIGS. 10a-10e schematically show a method of using the insert 20 of FIGS. 9a-9e for use with a screw 3' with a clavicle plate 1 as shown in FIG. 2a. Of course, the same procedure could be performed with embodiments of the clavicle plate 1 and/or the insert 20 other than the ones shown herein and/or on other bones than shown herein. Furthermore, the plate 1 is shown without bone for overview purposes (see FIGS. 20a+20b). The procedure is typically performed after the screws 3 have been screwed into a bone.

Figures 10A, 10B:
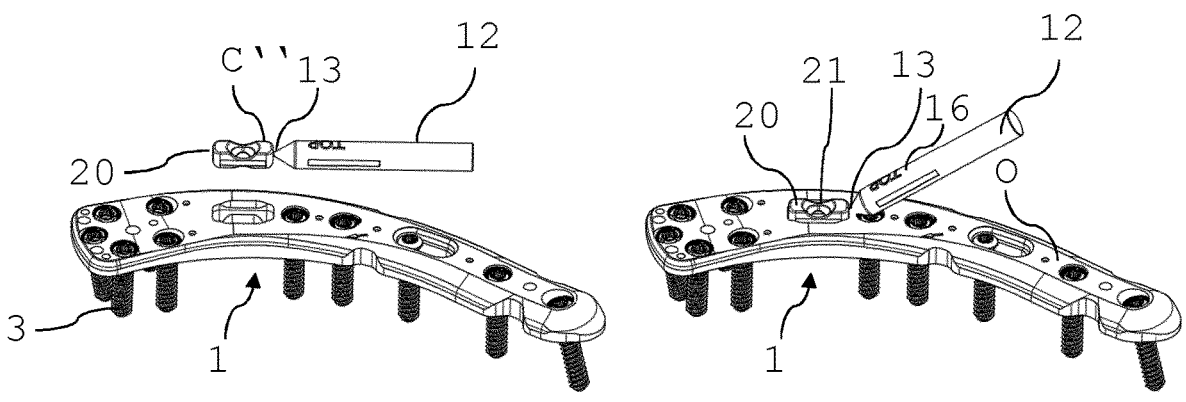
FIGS. 10a-10e: method steps for using the clavicle plate of FIG. 2 with the insert of FIGS. 9a-9e.

FIG. 10a shows the plate 1 with screws 3 screwed into screw holes 7,8. The insert 20 is essentially the same as in FIGS. 9a9e.

FIG. 10b shows how the insert 20 is inserted into a receptacle 6 provided for this purpose. The marking 16 indicates how the insert must be oriented, i.e. with the marking "TOP" 16 pointing in the same direction as the top side O of the plate 1. However, it is possible to swivel the insert 20 in the receptacle 6. In this case, the opening 21 can be oriented so that a screw 3 inserted into it can be screwed into a bone at a desired angle. By bending the holder 12 away, the predetermined breaking point 13 can be broken and the insert 20 is thus separated from the holder 12.

Figures 10C, 10D:
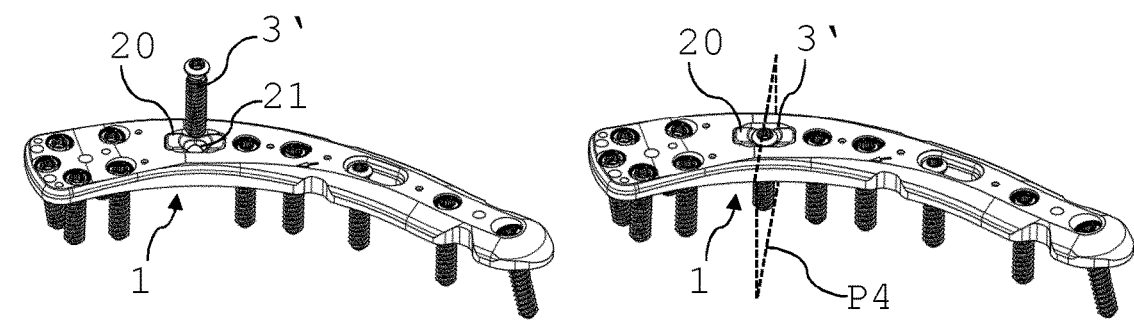

FIG. 10c shows how a screw 3' is inserted into the opening 21 of the insert 20.

FIG. 10d shows how the screw 3' has been fully inserted into the opening 21 of the insert 20.

Figure 10E:
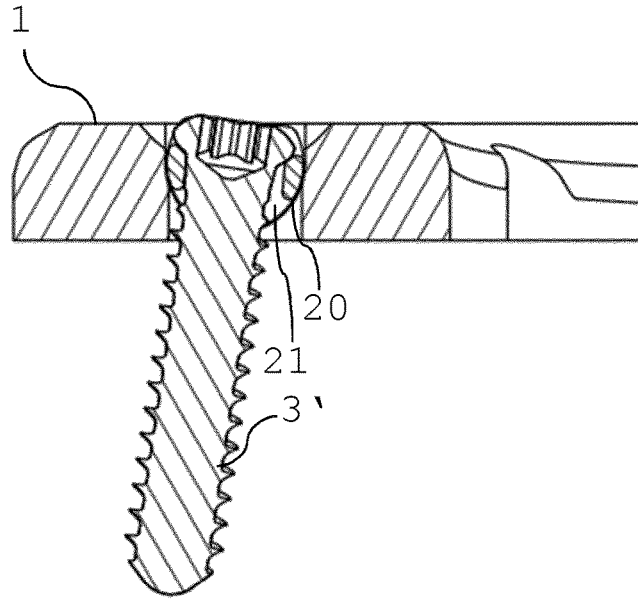

FIG. 10e shows a cross-section of the insert 20, the screw 3' and the plate 1 of FIG. 10d in the plane P4. The screw 3' is oriented at an angle to the plate 1 because the insert 20 has been pivoted in the receptacle 6. The opening 21 of the insert 20 is designed in such a way that the screw 3' has clearance in the opening 21 and could also be pivoted relative to the opening 21 and the insert 20 if required. This is also achieved in particular by the opening having a larger diameter than the shaft of the screw 3'.

Figure 11A:
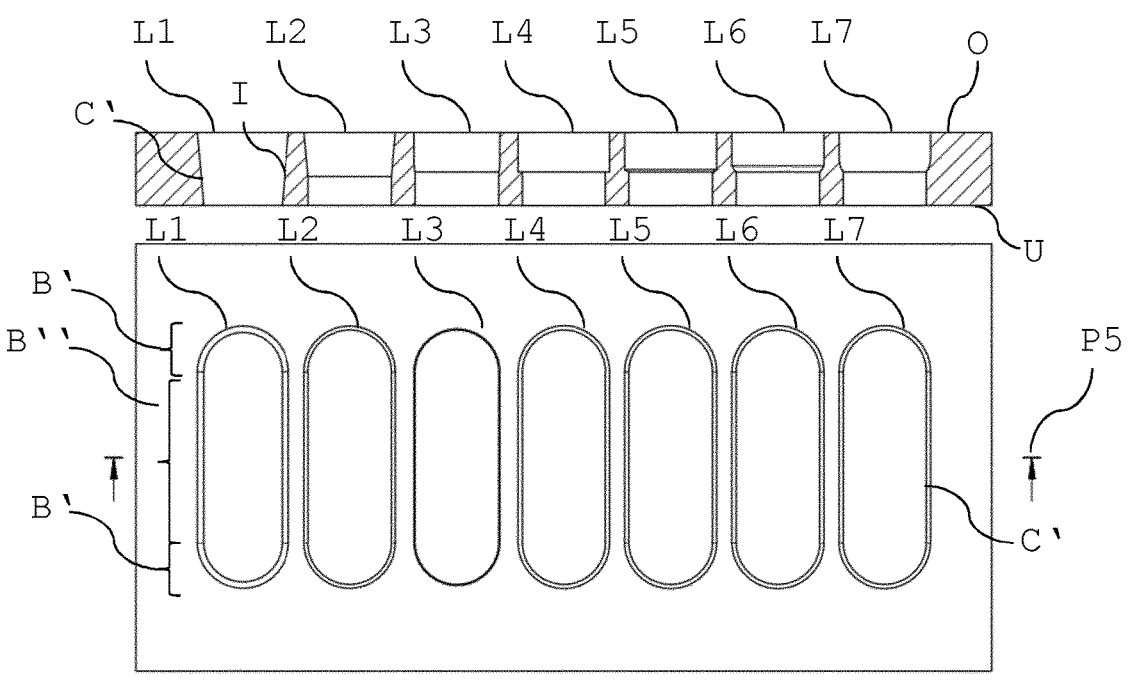
FIGS. 11a+11b: Various embodiments of a receptacle for an insert, each shown with and without insert, in a top view and a cross-sectional view, in which the insert is shown slightly tilted in each case.

FIG. 11a shows various receptacles L1, L2, L3, L4, L5, L6, L7, L8. These are not shown in a clavicle plate 1 for better illustration and overview. However, any of the receptacles L1, L2, L3, L4, L5, L6, L7, L8 shown could be combined with any of the clavicle plates 1 described herein, particularly those of FIGS. 1a and 2a, and are suitable for receiving an insert 10,20. The receptacles L1, L2, L3, L4, L5, L6, L7, L8 are shown below in a plan view. Directly above, a cross-section of each receptacle L1, L2, L3, L4, L5, L6, L7, L8 is shown in the plane P5. All receptacles L1, L2, L3, L4, L5, L6, L7, L8 are each rounded at two end sections B'. A middle section B", on the other hand, has a straight section in plan view, in particular with two mirror-symmetrical side walls.

All receptacles L1, L2, L3, L4, L5, L6, L7, L8 have in common that an inner wall I tapers at least partially from a top side to a bottom side. In addition, the end section B' is rounded, and the middle section B" is straight in plan view with mirror-symmetrical side surfaces.

The receptacle L1 has a trapezoidal cross section in the central region B". The inner walls I in the central region B' are shaped as straight surfaces which are at an angle to each other so that they taper from the top side O to the bottom side U. The inner walls I in the central region B" are shaped as straight surfaces which are at an angle to each other so that they taper from the top side O to the bottom side U. The receptacle L1 is thus shaped like a prism in the central region B".

Receptacle L2 is not shaped in a tapered manner in the area adjacent to the underside U. Instead, the inner walls I in the central area B" are partially shaped parallel to each other (in the area adjacent to the underside U). Directly above this, in the region adjacent to the top side O, the receptacle has essentially the same shape as the receptacle L1.

Receptacle L3 has a partially spherical and a partially cylindrical inner surface I. The radius of curvature of the spherical inner surface I corresponds to the radius of curvature of the outer contour C" of insert 1 (see FIG. 11b).

Receptacle L4 has a cross-section corresponding to two rectangles. The rectangle on the top side O is wider. The two areas with different widths are separated by a boundary surface parallel to the top side O. The two rectangles are arranged on the same side.

Receptacle L5 is similar to receptacle L4, but the two areas of different width are separated by an interface that is not shaped parallel to the top side O.

Figure 11B:
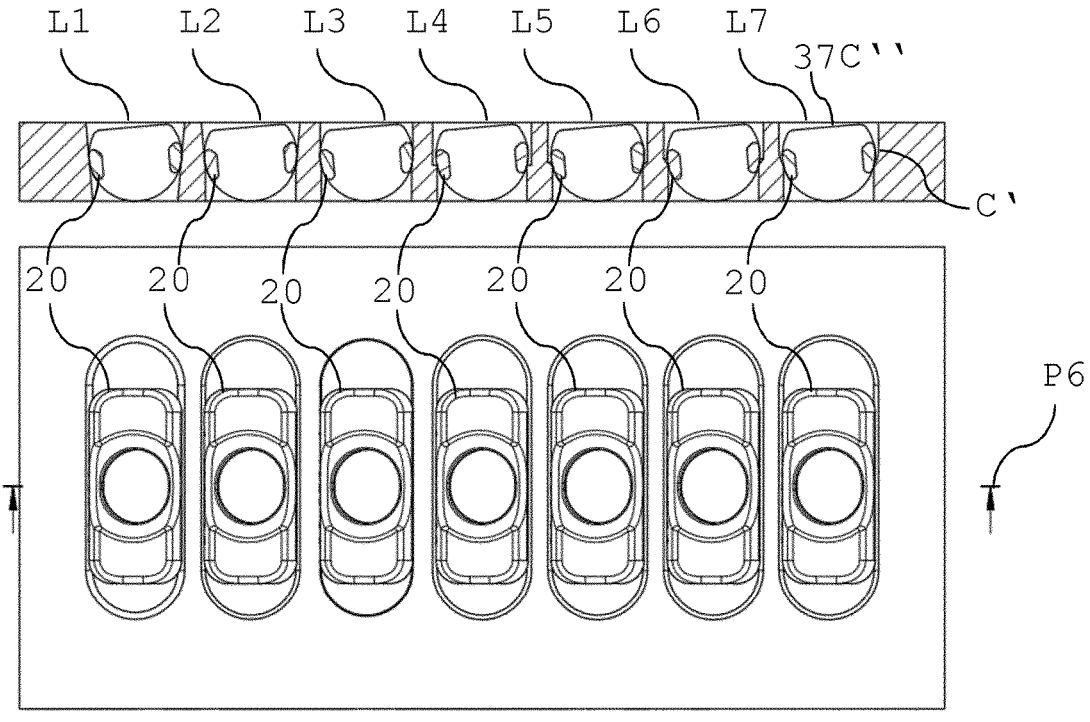

Receptacle L6 is similar to receptacle L3. However, the radius of curvature of the spherical inner surface I is different from the radius of curvature of the outer contour C" of the insert. Receptacle L7 is similar to receptacles L4 and L5, with the two areas of different width separated by an elliptical section. The shapes of the cross-sections shown here are only exemplary and could also have other shapes. In particular, hyperbolic, parabolic and/or multi-stepped designs are conceivable. FIG. 11b shows receptacles L1, L2, L3, L4, L5, L6, L7, L8 of FIG. 11a with an inserted insert 20 for receiving a screw. The exemplary insert 20 shown corresponds to the insert 20 of FIG. 9*a*, but any of the inserts 10,20 described here is suitable for receptacle in any of the receptacles 6, L1, L2, L3, L4, L5, L6, L7, L8 shown. The outer contour C'' of the inserts 20 is shaped in a rounded manner. The cross-section of the insert 20 perpendicular to its longitudinal axis is a segment of a circle, as the insert 20 comprises a milled-off portion 37 which is substantially straight. The rounded outer contour C' of the insert 20 is therefore adapted to all of the shown inner contours C'' such that the insert 20 can be pivoted in a plane perpendicular to the longitudinal axis of the insert 20 and the receptacle L1, L2, L3, L4, L5, L6, L7, L8. In addition, the insert is slidable along the longitudinal axis of the receptacle 6 and cannot slip through the receptacle.

Alternatively, an insert 10,20 with a different shape, for example an angular shape, could be inserted into the receptacles L3, L6, L7 shown in FIGS. 11*a* and 11*b*. The pivotability would be ensured thanks to the partially rounded inner contour C' of the receptacle L3, L6, L7.

FIGS. 12*a*-12*l* show various inserts 10 for suture fixation, which are suitable for receptacle in a screw hole 7 according to WO 2006/099766. The use of the inserts shown in FIGS. 12*a*-12*l* therefore does not require a specifically adapted receptacle 6.

The inserts 10 shown in FIGS. 12*a*-12*l* are adapted to be screwed into a conventional screw hole of a plate. For this purpose, they have a locking area according to WO 2006/099766 and a receptacle for a tool. Preferably, the receptacle is designed as a Torx drive. The insert 10 is adapted for holding a suture and preferably has at least one bore and/or a head with an undercut for this purpose. Preferably, the interlocking region is shaped such that, when screwed in, there is at least one region with a distance to the inner shape of a screw hole through which a suture can be guided. Preferably, the head has at least one recess through which a suture can be guided. In particular, such an insert makes it possible to fix a suture by means of a knot, so that the knot is arranged sunk in a screw hole.

Figures 12A, 12B, 12C, 12D, 12E, 12F, 12G, 12H:
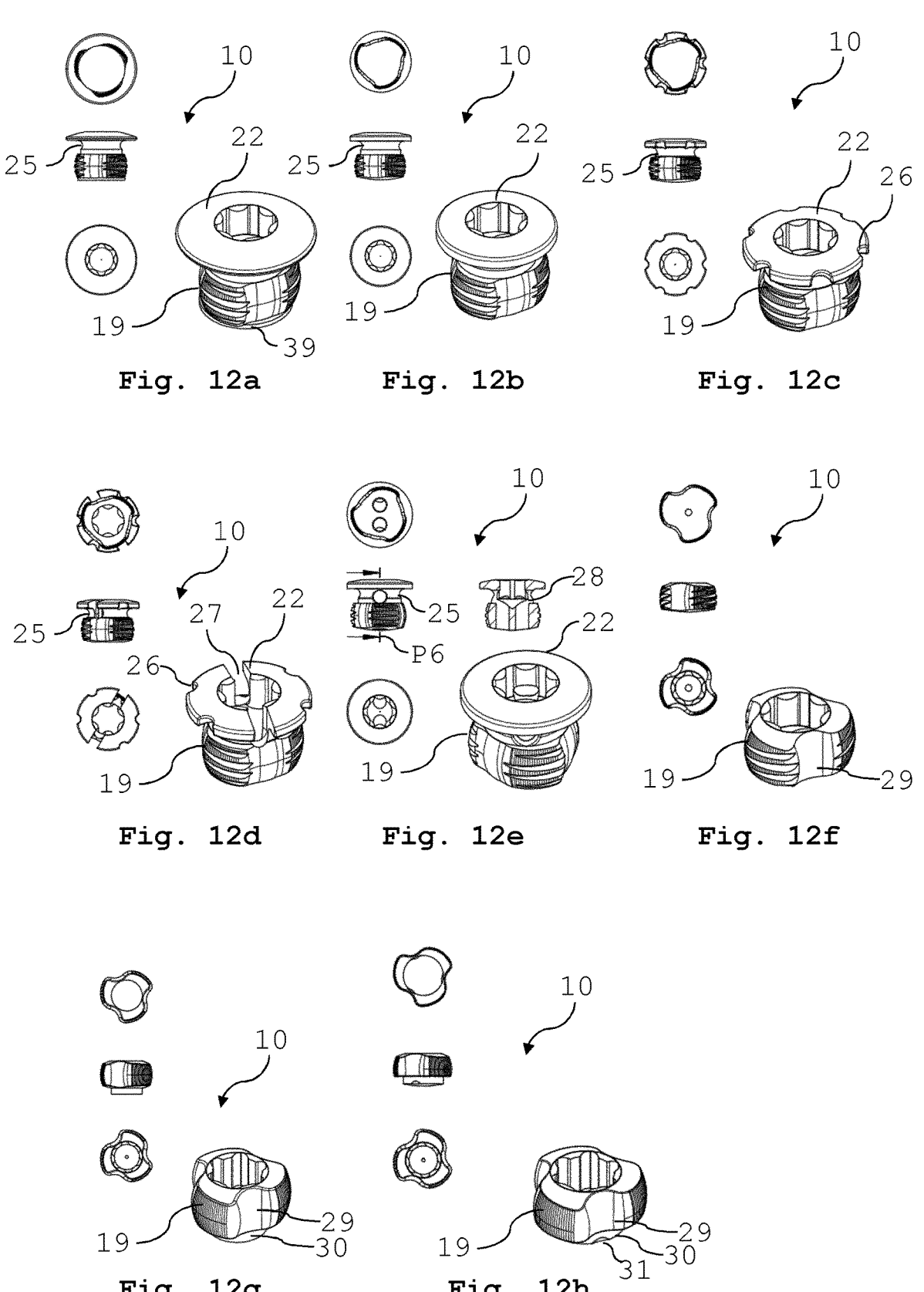
FIGS. 12a-12l: Various alternative inserts to be received in a screw hole and to be fixed to a suture, each shown in a side view, bottom view, top view, and perspective view.

FIG. 12*a* shows an embodiment of an insert 10 with a locking area 19 for receiving into a variable-angle screw hole 7 as shown in WO 2006/099766. The insert 10 can therefore be inserted into a screw hole at different angles. It comprises a head portion 22, and a neck portion 25 adjacent thereto, which comprises a centering collar to which a suture can be attached, and which is connected to the interlocking portion 19 via a circular cylindrical section. In this embodiment, the suture is guided over the plate edge. The insert shown here has a centering collar 39 on the underside. This allows the insert to align itself in a hole according to the hole axis and runs less risk of being tipped off when the suture is pulled.

FIG. 12*b* shows an insert 10 similar to the insert 10 shown in FIG. 12*a*. The neck area is spherical in this case. In this version, the suture is guided over the plate edge. In contrast to the design shown in FIG. 12*a*, the insert shown here does not have a centering collar.

FIG. 12*c* shows another embodiment of an insert 10 for suture fixation. It includes a head portion 22 and a curved neck portion 25 directly adjacent to the interlocking portion 19. Thus, the insert 10 shown lacks a circular cylindrical portion (see FIGS. 12*a* and 12*b*), allowing a suture held at the neck portion 25 to be sunk into a screw hole 7 if necessary. The head portion 22 includes six indentations 26 through which the suture can be passed, particularly when the insert is sunk. In this embodiment, the suture can be guided over the edge of the plate.

FIG. 12*d* shows an insert 10 similar to that shown in FIG. 12*c*. The head portion 22 includes four indentations and a slot 27. The insert is pierced, i.e., the suture can be passed through the bone. The slot 27 allows the suture to pass to the side of the screwdriver blade when the insert is screwed into the plate hole and allows the suture to be subsequently secured to the neck of the insert.

FIG. 12*e* shows an insert 10 that is similar to the insert 10 shown in FIG. 12 and further comprises two bores 28. The two holes are symmetrical with respect to the plane P6 and run parallel to the plane P6 in the interlocking area 19. In the neck portion 25, the holes 28 are perpendicular to the holes in the interlocking portion 19, making this insert 10 suitable for receiving a suture through one hole 28 so that it can be wrapped around the neck portion 25 and exited through the other hole 28. Likewise, this arrangement allows for the insertion of a screwdriver blade.

FIG. 12*f* shows an insert 10 used for the non-locking variable angle arrangement in a screw hole 7 (as shown in WO 2006/099766). Suture fixation can be performed by passing a suture laterally past the insert 10 between two interlocking sections 29. By anchoring the insert 10 in a plate (not shown) by means of the interlocking section 19, the suture is held laterally and can be held above the insert, for example by a knot.

FIG. 12*g* shows an insert 10 similar to the one shown in FIG. 12*f*. This insert 10 additionally comprises a collar 30 for better gripping of the insert during production on a machine.

FIG. 12*h* shows an insert 10 similar to the one shown in FIG. 12*g*. This insert additionally has a recess 31 at the collar 20, which allows a suture to be inserted into a screw hole 7 after screwing and thus to be guided into the section 29 between the interlocking areas without causing injury.

Figures 12I, 12J:
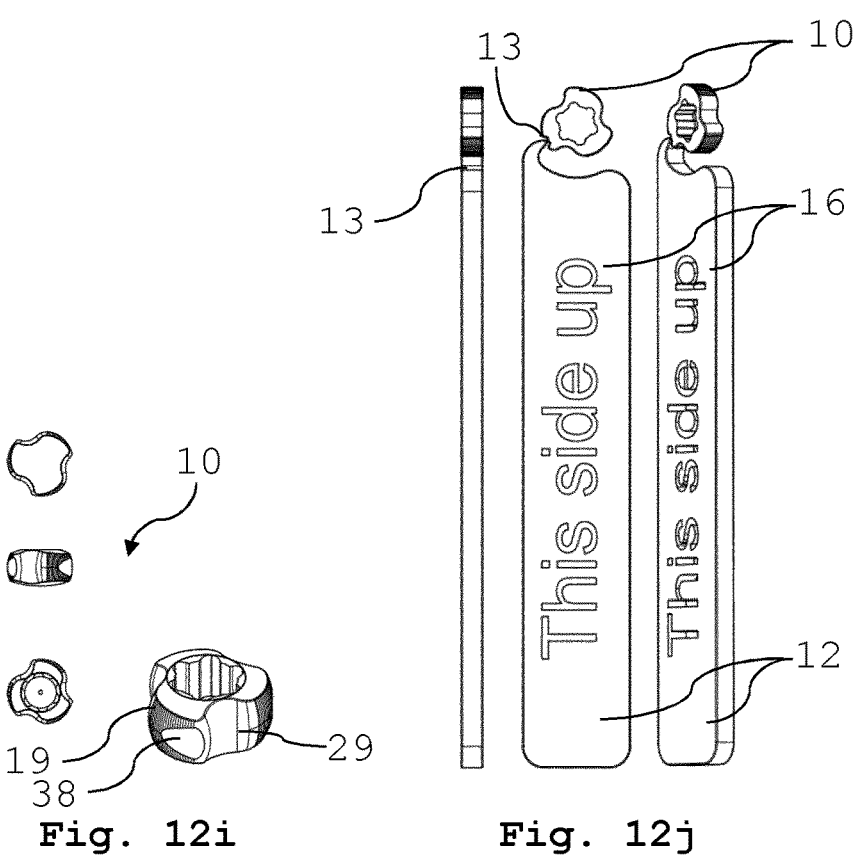

FIG. 12*i* shows an insert 10 similar to the one shown in FIG. 12*f*. It additionally includes a milled recess 38 in the interlocking area 19 for better gripping during production on a machine.

FIG. 12*j* shows a further embodiment of an insert 10 that can be inserted into a conventional screw hole 7 for suture fixation. This is connected to a holder 12 via a predetermined breaking point 13. This is formed by laser cutting as a cutout from a metal sheet and further comprises a marking 16 which serves to orient the insert 10 in a screw hole 7.

Figures 12K, 12L:
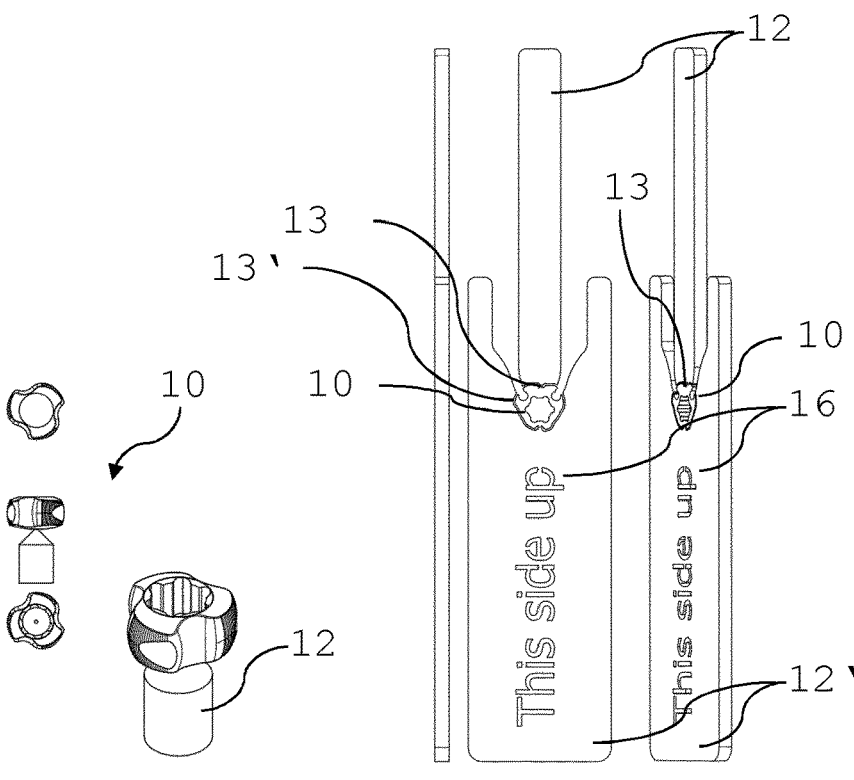

FIG. 12*k* shows an insert 10 that is designed essentially like the insert 10 shown in FIG. 12*i*. It additionally comprises a holder 12 which can be bent away from the insert 10 for separation.

FIG. 12*l* shows an insert 10 similar to that shown in FIG. 12*j*. The holder 12, 12' comprises two parts, each of which is connected to the insert 10 via a predetermined breaking point 13, 13'. The two-piece holder 12, 12' is formed from a sheet by laser cutting.

The insert in FIG. 12*l* has two holders. Together, the holders form a guide for a suture that can preferably be held on the insert. Both holders are connected to the insert via a predetermined breaking point so that they can be broken independently of each other. Preferably, the insert has a recess in which a suture can be received. Particularly preferably, the suture in the recess cannot be removed without force.

Figure 13:
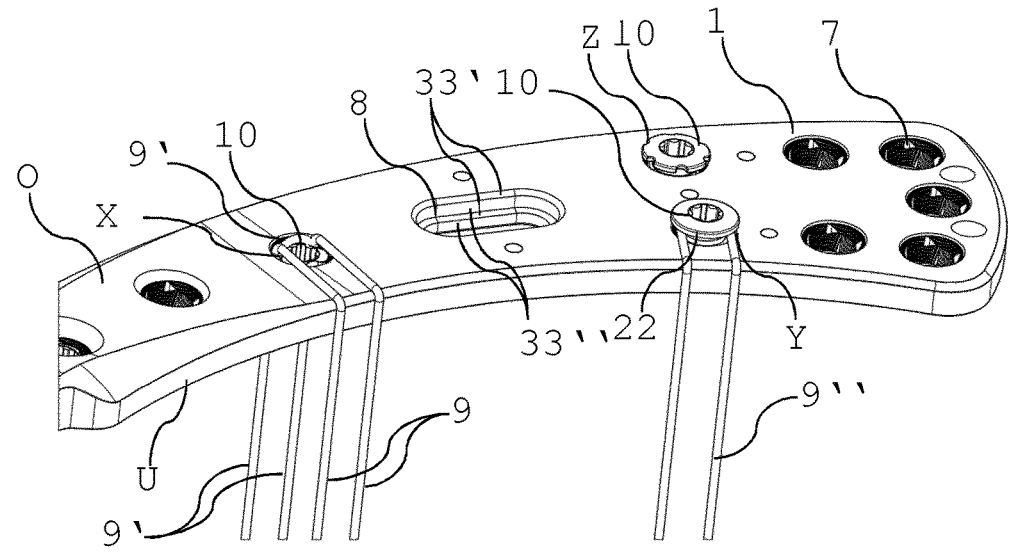
FIG. 13: the use of a clavicle plate with inserts of FIGS. 12a, 12c and 12f.

FIG. 13 schematically shows the use of inserts 10 of FIG. 12 for suture fixation in a conventional screw hole 7 in a clavicle plate.

The clavicle plate 1 includes oblong hole 8 in addition to multiple screw holes 7.

The insert 10 of FIG. 12*f* is inserted at a position X. Alternatively, an insert of FIGS. 12*g*-12*l* could be used analogously. This anchors two sutures 9,9', each inserted from one side as a suture loop into the plate hole. After screwing in the insert, they are protected against loss and the suture 9 is guided over the plate edge where it can be knotted, for example. The suture 9' is fixed in the plate hole in the same way, but in the opposite direction, and is therefore not guided over the plate edge. Alternatively, the sutures 9,9' could be guided through the bone, protected against loss by means of an insert in the plate hole and knotted over the insert.

At a position Y, the insert 10 of FIG. 12*a* is inserted. The suture 9" comprises a loop which is anchored in the neck area 25 of the insert 10. For a better overview, the insert 10 is shown in a not completely screwed-in state. By screwing it in further, the suture 9" can be pressed against the top of the plate O. The suture 9 is guided over the top of the plate O and one edge of the plate 1.

The insert 10 of FIG. 12*c* is screwed in at position Z. For a better overview, this insert is shown without suture.

FIGS. 14*a*-14*h* schematically show a method of using the insert 10 of FIG. 12*l*.

Figures 14A, 14B:
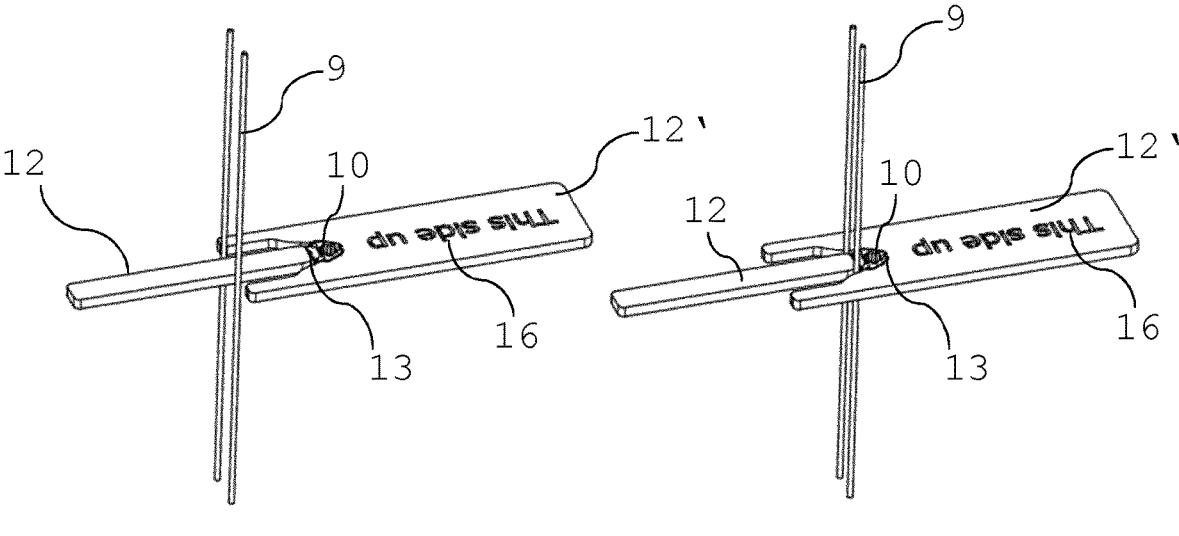

FIG. 14*a* shows two sutures 9 that are fed along the first section of the one-piece holder 12, 12', which comprises two cutoffs, through one insertion slot each to the side of the insert 10. The respective insertion slot is formed between the two pieces of the holder 12, 12'. At this point, the sutures 9 may have already been held to a bone and passed through the clavicle and a clavicle plate (not shown).

FIG. 14*b* shows how the sutures 9 are guided closer to the insert 10.

Figures 14C, 14D:
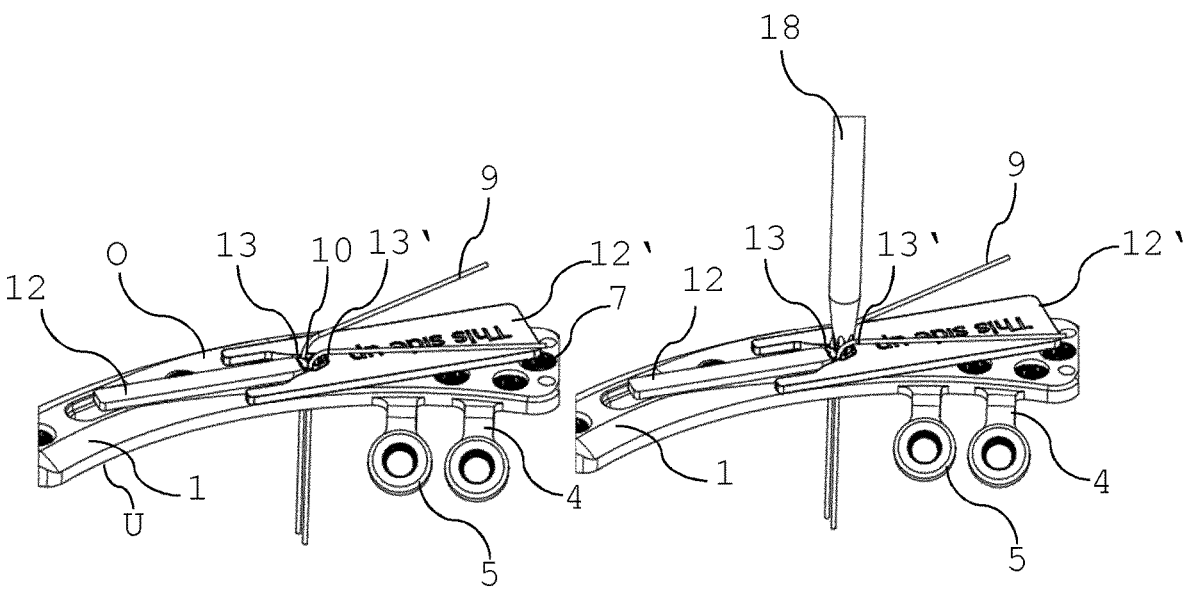

FIG. 14*c* shows how the insert is placed against the clavicle plate 1 so that the insert 10 is positioned over the desired screw hole 7. The sutures 9 are tightened so that they snap into the insert 10. The insert 10 is positioned so that the marking 16 points upward (in a direction from the bottom of the plate to the top of the plate O).

FIG. 14*d* shows how a blade 18 of a screwdriver is inserted into the insert.

Figures 14E, 14F:
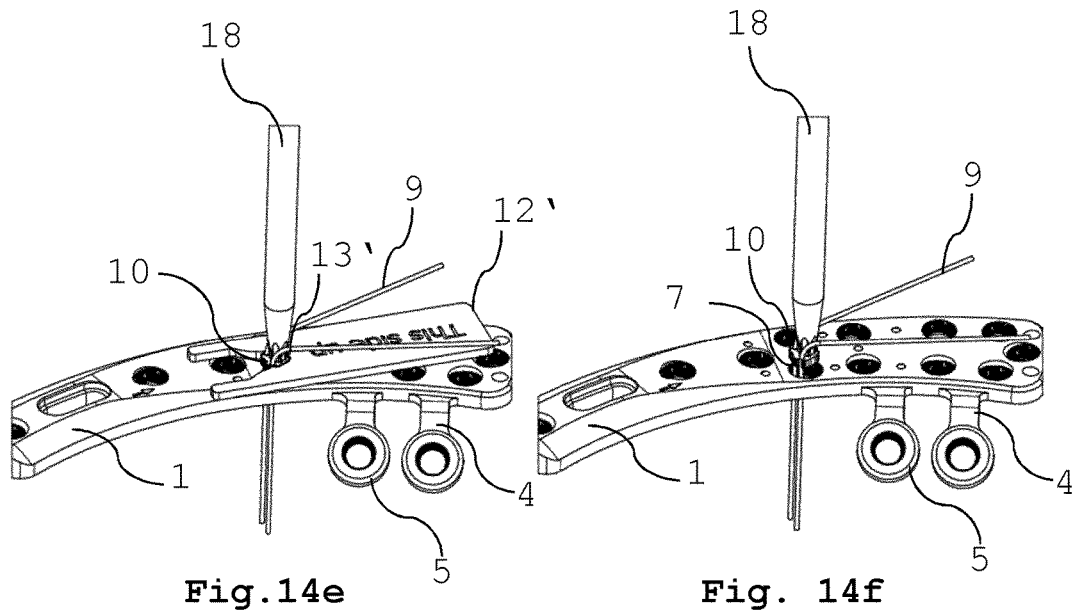

FIG. 14*e* shows how the first piece 12 of the holder is broken at the predetermined breaking point 13 and removed.

FIG. 14*f* shows how the second piece 12' of the holder is also broken off at the other predetermined breaking point 13' and removed. The insert 10 can be held in this state with the aid of the blade 18.

FIG. 14*g* shows how the insert 10 is screwed into the desired screw hole using the blade 18.

FIG. 14*h* shows the plate 1 with the insert 10 screwed in, whereby the sutures 9 are guided laterally past the insert. These could, for example, be held above the insert by means of a knot (not shown).

Figure 15:
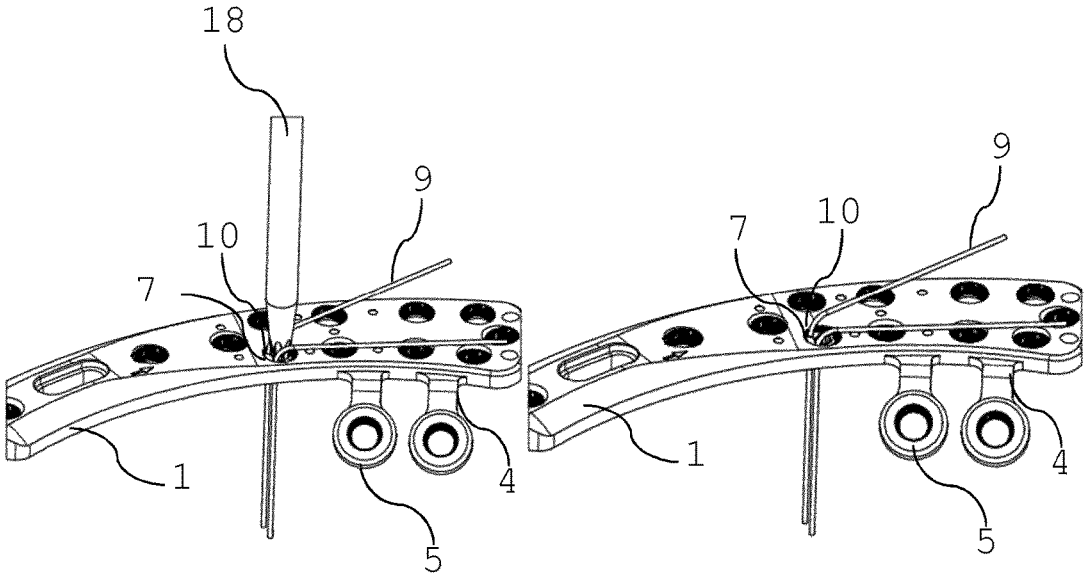
FIG. 15: a second embodiment of an insert for suture fixation.
Figure 15:
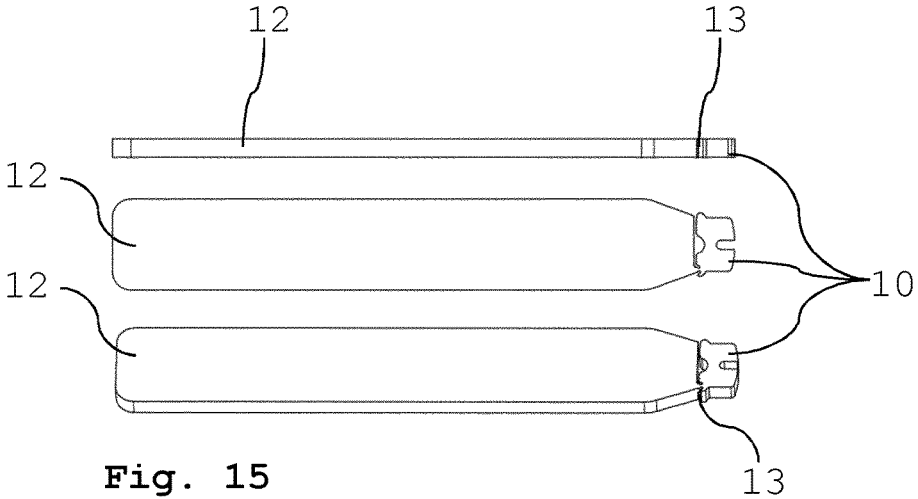

FIG. 15 shows another embodiment of an insert 10 for suture fixation in a conventional screw hole. This comprises a holder 12 which is connected to the insert 10 via a predetermined breaking point 13. It is shaped to be pressed into a screw hole along a longitudinal axis of the holder.

FIGS. 16*a*-16*d* schematically show a method of using the insert 10 of FIG. 15.

Figures 16A, 16B:
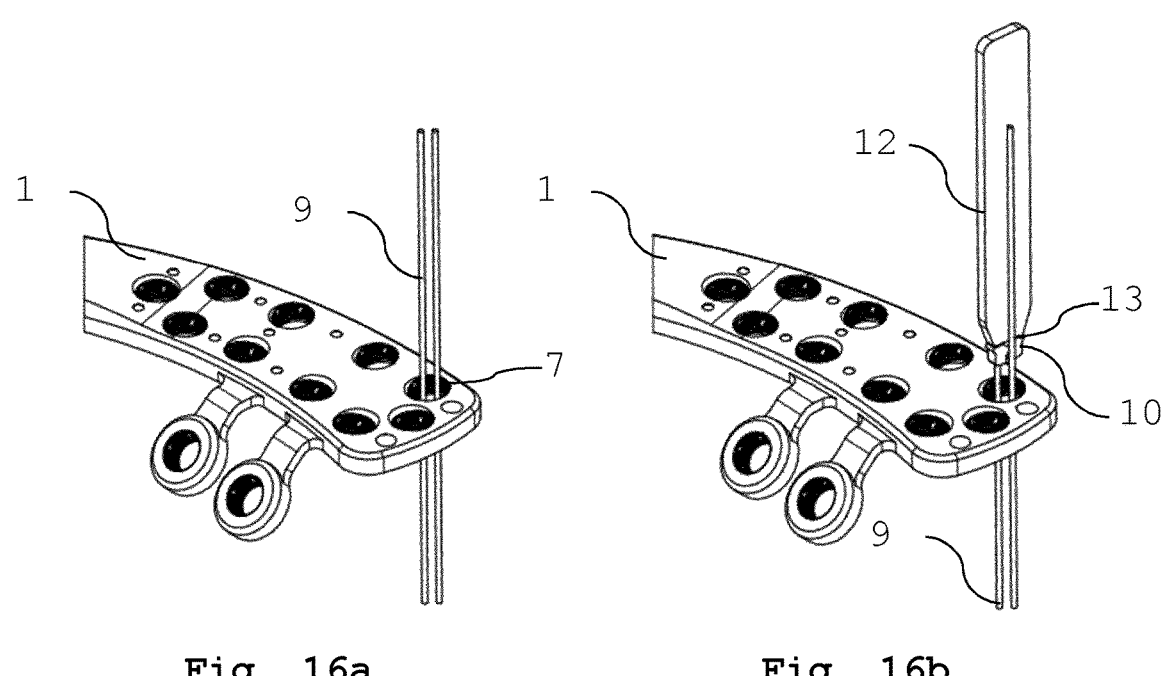
FIGS. 16a-16d: the steps of a method for using the insert of FIG. 15.

FIG. 16*a* shows how, in a first step, two sutures 9 are passed through a screw hole 7.

FIG. 16*b* shows how the insert 10 is guided between the two sutures towards the screw hole 7.

Figures 16C, 16D:
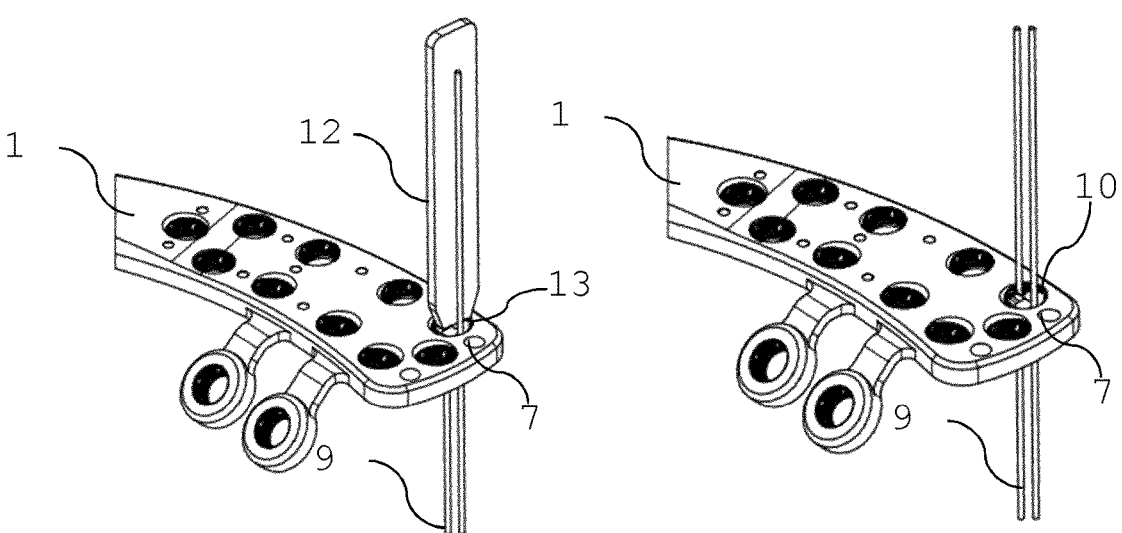

FIG. 16*c* shows the pressing-in of the insert 10 into the screw hole 7, whereby it is fixed rotationally securely in this screw hole 7. During pressing-in, the insert 10 is compressed and the insert then holds frictionally in the plate hole 7. The stage shown here is particularly suitable for removing the retainer 12 by breaking the predetermined breaking point 13.

FIG. 16*d* shows the plate 1 with the inserted insert 10 after removal of the holder. The two sutures 9 can be tied together by a knot above the insert 10 and therefore wrap around the insert 10 in such a way that the sutures 9 are retained on the insert 10. At the same time, the pull of the sutures prevents the insert from sliding out of the plate hole.

Figures 17A, 17B, 18A, 18B, 18C, 18D:
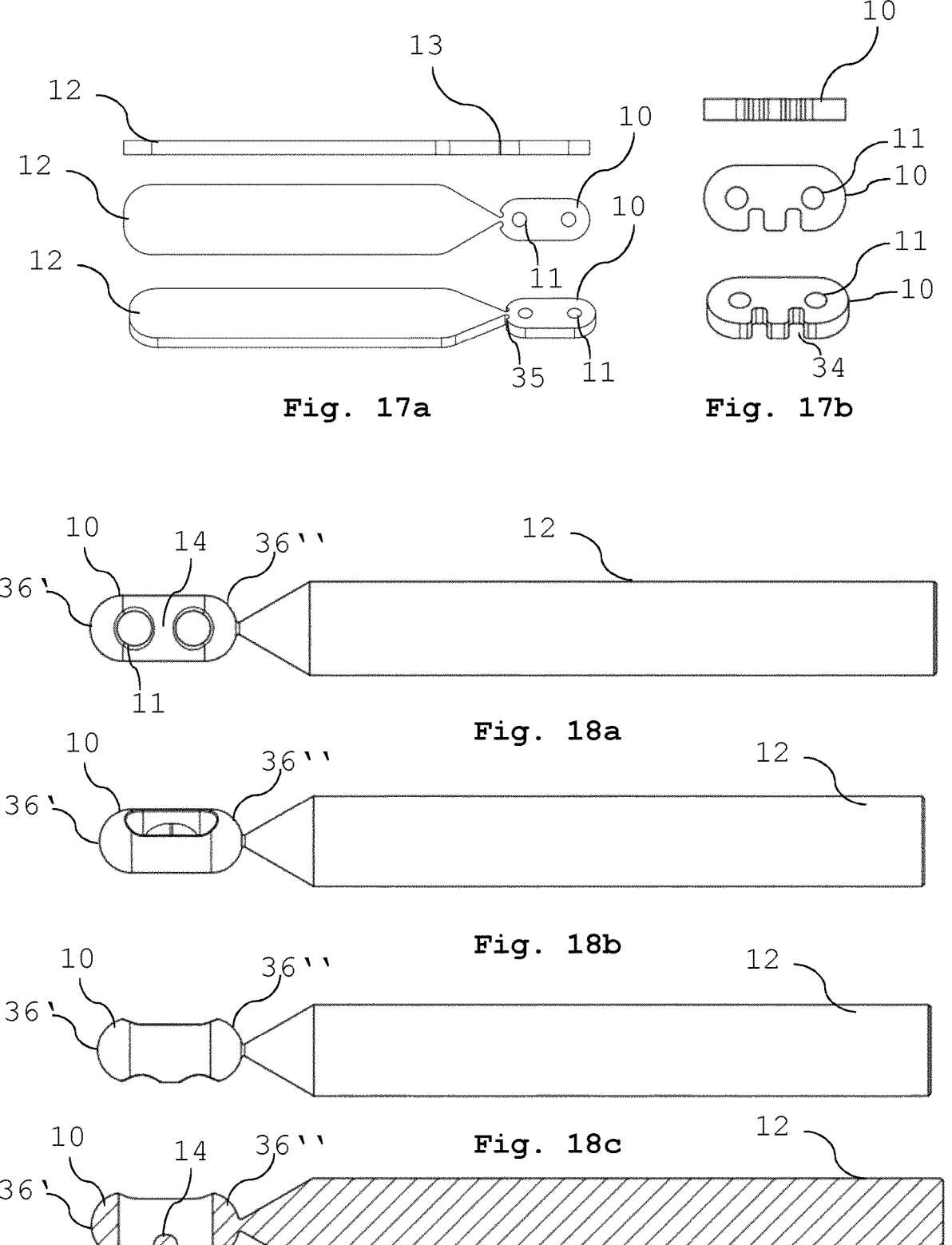
FIGS. 17a+17b: a third and fourth embodiment of an insert for suture fixation in a side view, top view and perspective view.
FIGS. 18a-18g: a fifth embodiment of an insert for suture fixation in a top view, perspective view, side view and cross-sectional view.

FIG. 17*a* shows a further embodiment of an insert 10 for suture fixation in a side view, top view and perspective view. The insert shown is adapted for use in a specially designed receptacle (for example 6 in FIG. 1*a*). The insert 10 includes a retainer 12 connected to the insert 10 by a predetermined breaking point. The insert is substantially flat in design and has a partially rounded shape. The insert 10 has two holes 11 through which a suture can be passed. At the predetermined breaking point 13, the insert has a recess 35 in the direction of the holes 11. As a result, any irregularities on the surface resulting from breaking of the predetermined breaking point 13 are recessed and do not come into contact with the receptacle for the insert 10.

FIG. 17*b* shows another variant of an insert 10, which is designed without a holder. However, it would be conceivable to equip this insert with a holder connected, for example, via a predetermined breaking point. The insert 10 shown is similar to the one shown in FIG. 17*a*. In addition to the aforementioned missing holder, this insert also has a lateral recess 34 compared to the one shown in FIG. 17*a*, at which the insert can be gripped by means of a tool (tweezers or other holding instrument).

FIG. 18*a* shows a further embodiment of an insert 10 for suture fixation in a bottom view. The insert 10 is similar to the insert 10 of FIGS. 6*a*-6*e*. However, it includes spherical sections 36',36" at the ends. A spherical section 36" is connected to a support via a predetermined breaking point 13. A strut 14 forms two openings 11 through which a suture (not shown) can be passed. The strut 14 is flush with the surface of the insert 10 on the underside. The insert also has no flattening on the upper side.

FIG. 18*b* shows the insert 10 of FIG. 18*a* in a perspective view.

FIG. 18*c* shows the insert of FIG. 18*a* in a side view.

FIG. 18*d* shows the insert of FIG. 18*a* in a cross-sectional view in a plane parallel to a longitudinal axis of the insert 10 and the holder 12. The strut 14 is sunk and forms two openings 11 through which a suture 9 can be passed.

Figures 18E, 18F, 18G, 19A, 19B, 19C, 19D:
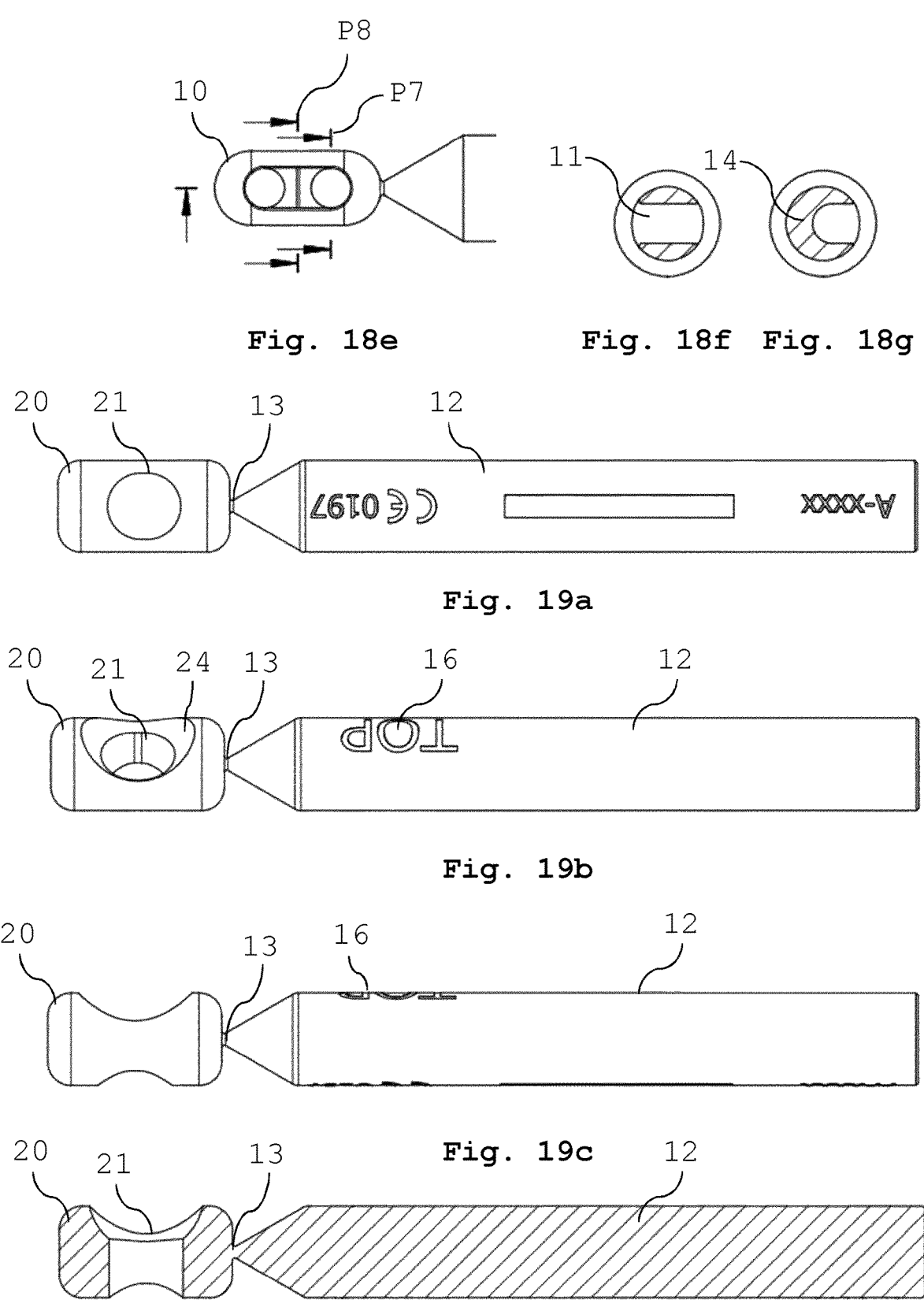
FIGS. 19a-19d: a sixth embodiment of an insert for receiving a screw in a top view, perspective view, side view as well as in a cross-sectional view along the longitudinal axis.

FIG. 18*e* shows a detailed view of the insert 10 of FIG. 18*a*.

FIG. 18*f* shows a cross-section of the insert 10 of FIG. 18*a* in the plane P7 (see FIG. 18*e*) with one of the openings 11 for the passage of a suture. The opening 11 is substantially cylindrical in shape. The insert 10 has a substantially circular cross-section. However, it would also be conceivable to shape the insert 10 straight on one side so that the cross-section has the shape of a segment of a circle (as is the case, for example, with the insert of FIGS. 6*a*-6*e*).

FIG. 18*g* shows a cross-section of the insert 10 of FIG. 18*e* in the plane P8 passing through the strut 14. The strut 14 is shaped flush with the outside of the insert 10 and sunk.

FIG. 19*a* shows another variant of an insert 20 for fixing a screw. It comprises an opening 21, which is designed here without a thread and which is adapted for the receptacle of a screw. It is connected to a holder 12 via a predetermined breaking point 13.

FIG. 19*b* shows the insert 20 of FIG. 19*a* in a perspective view. The insert 20 is similar to that of FIGS. 9*a*-9*e*. However, like the insert 10 of FIGS. 18*a*-18*g*, it has a substantially circular cross-section in a plane perpendicular to a longitudinal axis of the holder 12 and the insert 20. Likewise, the insert does not have a flattening on its top side. The opening 21 is shaped with a recess 24 on its top side, such that the opening 21 is shaped as a countersunk hole for a screw.

FIG. 19*c* shows the insert 20 of FIG. 19*a* in a side view.

FIG. 19*d* shows the insert 20 of FIG. 19*a* in a cross-sectional view in a plane perpendicular to the longitudinal axis of the holder 12 and the insert 20.

Figure 20A:
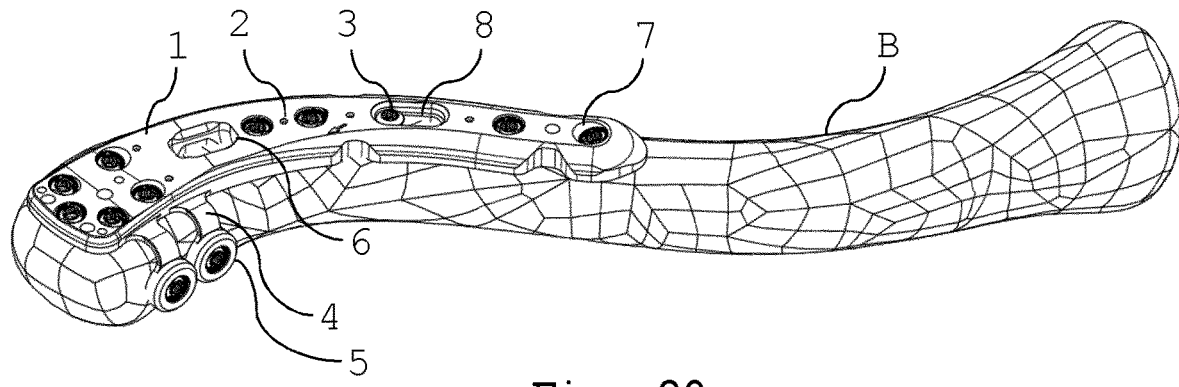
FIGS. 20a+20b: the clavicle plate of FIG. 1 fixed to a bone in a perspective view.

FIG. 20*a* shows the clavicle plate 1 of FIG. 1*a* in a condition screwed to a human clavicle B. The plate 1 is fixed with nine screws 3 in screw holes 7. In addition, two screws 3 are fixed to the bone via a tab 5 each, and another screw 3' is fixed via an oblong hole 8. The treatment shown here was performed without the use of an insert 10,20. However, it would be conceivable to insert an insert 10 into the receptacle 6 adapted for this purpose and to fix a suture or to screw a further screw 3 into the bone B via an insert 20.

Figure 20B:
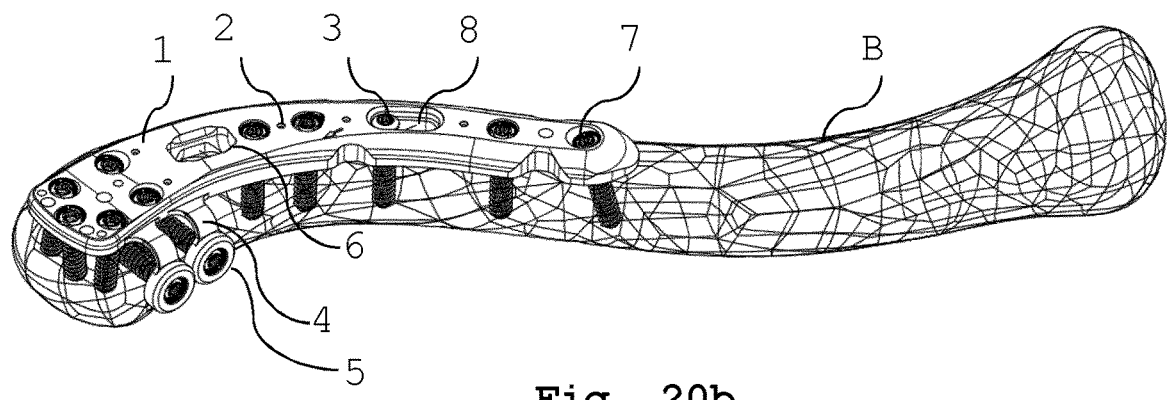

FIG. 20*b* shows the clavicle plate 1 of FIG. 20*a*, with bone B shown transparent for clarity.

The invention claimed is:

1. A kit comprising at least one insert and a plate for treatment of a bone, wherein the plate has a receptacle for the insert, wherein the insert has an outer contour, wherein the receptacle has an inner contour, wherein the outer contour and the inner contour are adapted to each other in such a way that the insert inserted into the receptacle can be pivoted about an axis which is substantially parallel to a plate upper side, wherein the insert inserted into the receptacle is displaceable in a longitudinal direction of the plate, wherein the insert is adapted for being attached to a bone with a connection mechanism, wherein the plate is adapted in size and shape to the bone, wherein the kit further comprises a suture for fixing to a body part, and wherein the insert is adapted for being attached to said suture.

2. The kit according to claim 1, wherein the outer contour of the insert and/or the inner contour of the receptacle is at least partially rounded.

3. The kit according to claim 1, wherein the insert comprises at least one strut for holding the suture.

4. The kit according to claim 3, wherein said at least one strut is sunk.

5. The kit according to claim 1, wherein the insert comprises a holder and is connected thereto via at least one predetermined breaking point.

6. The kit according to claim 1, wherein the plate has, on the plate upper side, at least one recess not penetrating the plate and adapted to temporarily receive a tool.

7. The kit according to claim 6, further comprising a tool, said tool comprising at least one tip, the size of which is adapted to be brought into operative engagement with the at least one recess of the plate.

8. The kit according to claim 1, wherein the plate has at least one screw hole for receiving a bone screw, wherein the plate has at least one overhanging tab at one end.

9. The kit according to claim 8, wherein the at least one overhanging tab is connected to the plate via at least one bendable bridge and wherein the at least one tab has a receiving opening for a bone screw.

10. The kit according to claim 9, wherein the plate has, in a region of at least one screw hole, a greater plate thickness than in the region of the at least one bendable bridge.

11. The kit according to claim 9, wherein the at least one overhanging tab is shaped such that an angle between a longitudinal axis of the receiving opening for a bone screw and a normal to a surface of the plate is at most 150°.

12. The kit according to claim 1, the plate having at least one screw hole for receiving a bone screw, wherein the plate further comprises a top side and a bottom side, the bottom side of the plate being adapted in its shape to be in contact with a bone, the plate having on its top side at least one recess which does not penetrate the plate and which is adapted for temporarily receiving a tool.

13. The kit according to claim 12, wherein the at least one recess is located, with respect to a longitudinal direction of the plate, between screw holes.

14. The kit according to claim 12, wherein the at least one recess is arranged on the top side in a transverse direction perpendicular to a longitudinal direction substantially central to an outer boundary of the plate.

15. The kit according to claim 12, wherein the at least one recess has a longitudinal axis and is shaped substantially rotationally symmetrical with respect to the longitudinal axis.

16. The kit according to claim 1, wherein the plate has at least one screw hole, wherein the screw hole is separate from the receptacle for the insert.

17. The kit according to claim 16, wherein the plate has an elongated shape.

\* \* \* \* \*